(12) United States Patent
Wu et al.

(10) Patent No.: US 12,226,216 B2
(45) Date of Patent: Feb. 18, 2025

(54) SIGNAL PROCESSING APPARATUS AND SIGNAL PROCESSING METHOD

(71) Applicant: TSINGHUA UNIVERSITY, Beijing (CN)

(72) Inventors: Huaqiang Wu, Beijing (CN); Zhengwu Liu, Beijing (CN); Jianshi Tang, Beijing (CN); Bin Gao, Beijing (CN); He Qian, Beijing (CN)

(73) Assignee: TSINGHUA UNIVERSITY, Beijing (CN)

(*) Notice: Subject to any disclaimer, the term of this patent is extended or adjusted under 35 U.S.C. 154(b) by 848 days.

(21) Appl. No.: 17/412,016

(22) Filed: Aug. 25, 2021

(65) Prior Publication Data

US 2022/0061729 A1    Mar. 3, 2022

(30) Foreign Application Priority Data

Aug. 27, 2020   (CN) .......................... 202010878572.5

(51) Int. Cl.
    *G11C 13/00*    (2006.01)
    *A61B 5/00*    (2006.01)
    (Continued)

(52) U.S. Cl.
    CPC ................ *A61B 5/304* (2021.01); *A61B 5/31* (2021.01); *A61B 5/4094* (2013.01);
    (Continued)

(58) Field of Classification Search
    CPC ... G11C 11/54; G11C 2213/79; G11C 7/1006; G11C 13/0028; G11C 13/004; G11C 13/0069; G11C 16/0483; G11C 13/0026; G11C 13/003; G11C 5/063; G11C 7/18; G11C 11/1673; G11C 11/223; G11C 5/02; G11C 13/0004; G11C 16/0466;
    (Continued)

(56) References Cited

U.S. PATENT DOCUMENTS 10,482,929 B2 * 11/2019 Li .......................... G06N 3/065
2020/0237311 A1    7/2020 Li et al.

FOREIGN PATENT DOCUMENTS

CN    109800729 A    5/2019

OTHER PUBLICATIONS

Office Action (and translation) of Corresponding Chinese Application No. 202010878572.5, mailed Mar. 3, 2022, pp. 1-16.

* cited by examiner

*Primary Examiner* — Thong Q Le
(74) *Attorney, Agent, or Firm* — Loeb & Loeb LLP

(57) ABSTRACT

A signal processing apparatus and a signal processing method are provided. The signal processing apparatus includes a memristor array, an input circuit, a first switching circuit, a second switching circuit, an output circuit, and a control circuit. The memristor array includes memristor units and is connected to source lines, word lines and bit lines. The control circuit is configured to control the first switching circuit to select at least one source line to apply at least one first signal to the at least one source line respectively, control the second switching circuit to select and activate at least one word line to apply the at least one first signal to a memristor unit corresponding to the at least one word line, and control the output circuit to output a plurality of second signals based on conductivity values of memristors of the memristor array.

19 Claims, 11 Drawing Sheets

(51) Int. Cl.
*A61B 5/304* (2021.01)
*A61B 5/31* (2021.01)

(52) U.S. Cl.
CPC ...... *G11C 13/0026* (2013.01); *G11C 13/0028* (2013.01); *G11C 13/003* (2013.01); *G11C 13/004* (2013.01); *G11C 13/0069* (2013.01); *G11C 2213/79* (2013.01)

(58) Field of Classification Search
CPC ... G11C 16/26; G11C 11/161; G11C 11/5628; G11C 13/0097; G11C 16/3459; G11C 8/14; G11C 11/1657; G11C 11/2257; G11C 11/2273; G11C 11/40; G11C 13/0002; G11C 16/0425; G11C 16/08; G11C 2013/0042; G11C 5/025; G11C 11/1653; G11C 13/0007; G11C 13/0023; G11C 14/0063; G11C 16/3481; G11C 7/12; G11C 8/08; G11C 11/1693; G11C 13/0033; G11C 13/0061; G11C 17/00; G11C 2013/0045; G11C 2013/009; G11C 2213/82; G11C 7/06; G11C 7/08; G11C 7/1012; G11C 11/5685; G11C 13/00; G11C 16/0416; G11C 16/10; G11C 16/14; G11C 2013/0073; G11C 11/1675; G11C 11/4085; G11C 11/5621; G11C 11/5642; G11C 13/0019; G11C 13/0038; G11C 13/0064; G11C 16/0433; G11C 16/16; G11C 16/22; G11C 16/30; G11C 16/34; G11C 2013/0076; G11C 2213/15; G11C 27/005; G11C 7/16; G11C 7/222; G11C 7/24; G11C 11/2297; G11C 11/34; G11C 11/4097; G11C 11/5671
See application file for complete search history.

SIGNAL PROCESSING APPARATUS AND SIGNAL PROCESSING METHOD

CROSS REFERENCE TO RELATED APPLICATION

The application claims priority to the Chinese patent application No. 202010878572.5, filed Aug. 27, 2020, the entire disclosure of which is incorporated herein by reference as part of the present application.

TECHNICAL FIELD

The present disclosure relates to the technical field of signal processing, in particular to a signal processing apparatus and a signal processing method.

BACKGROUND

Recording the electrical activities of the brain through neural probes has important applications in the diagnosis and control of nervous system diseases such as epilepsy and Parkinson's disease, and in exploring the working mechanism of the brain. Processing the recorded neuroelectric signals in order to extract useful information is the premise of making good use of them. In recent years, in brain computer interface (BCI; or brain-machine interface, BMI; or Neural interface) and other application fields, the number of recording channels of neuroelectric signals shows a rapid growth trend, which makes the processing of multi-channel neural signals a major difficulty.

SUMMARY

At least one embodiment of the present disclosure provides a signal processing apparatus. The signal processing apparatus comprises a memristor array, comprising a plurality of memristor units and connected to a plurality of source lines, a plurality of word lines and a plurality of bit lines, wherein each of the plurality of memristor units comprises a memristor; an input circuit, configured to receive a plurality of first signals on a plurality of channels; a first switching circuit, connected with the plurality of source lines; a second switching circuit, connected with the plurality of word lines; an output circuit, connected with the plurality of source lines; and a control circuit, configured to control the first switching circuit to select at least one source line of the plurality of source lines to apply at least one first signal of the plurality of first signals to the at least one source line respectively, control the second switching circuit to select and activate at least one word line of the plurality of word lines to apply the at least one first signal to the memristor unit corresponding to the at least one word line, and control the output circuit to output a plurality of second signals based on conductivity values of memristors of the memristor array.

For example, in some embodiments, the signal processing apparatus further comprises a third switching circuit, connected with the plurality of bit lines, wherein before the at least one first signal is applied, the control circuit is further configured, in a first operation mode, to control the second switching circuit to select the plurality of word lines to apply a first voltage to the memristor units corresponding to the plurality of word lines, and control the third switching circuit to select the plurality of bit lines to apply a second voltage to the memristor units corresponding to the plurality of bit lines.

For example, in some embodiments, the control circuit is further configured, in a second operation mode, to control the second switching circuit to sequentially select and activate each of the at least one word line, so as to apply segments of the at least one first signal to the memristor unit corresponding to the at least one word line respectively, and control to apply a ground voltage to the plurality of bit lines.

For example, in some embodiments, the control circuit is further configured, in a third operation mode, to control the second switching circuit to sequentially select and activate the at least one word line of the plurality of word lines, so that the output circuit outputs the plurality of second signals through the at least one source line, and control to apply a ground voltage to the plurality of bit lines.

For example, in some embodiments, the control circuit is further configured, in a fourth operation mode, to control the second switching circuit to select the plurality of word lines to apply a first voltage to the memristor units corresponding to the plurality of word lines, and control the third switching circuit to select the plurality of bit lines to apply a second voltage to the memristor units corresponding to the plurality of bit lines.

For example, in some embodiments, the number of the at least one first signal is greater than or equal to 2, and the control circuit is configured to control the first switching circuit to select at least one source line of the plurality of source lines to apply each first signal of the at least one first signal to a corresponding source line respectively, and control the second switching circuit to select and activate at least one word line of the plurality of word lines to apply each first signal of the at least one first signal to the memristor unit corresponding to a corresponding word line.

For example, in some embodiments, the signal processing apparatus further comprises a preprocessing circuit, wherein the preprocessing circuit is configured to preprocess each original signal of a plurality of original signals to form the plurality of first signals with an amplitude within a predetermined range, and transmit the plurality of first signals to the input circuit.

For example, in some embodiments, the predetermined range is a resistance-change voltage range or a read voltage range of the memristor.

For example, in some embodiments, the preprocessing circuit comprises an amplification circuit and a bias circuit, wherein the bias circuit is configured to provide a bias signal, and the amplification circuit is configured to process the original signal based on the bias signal to form the plurality of first signals with the amplitude within the predetermined range.

For example, in some embodiments, the signal processing apparatus further comprises a classifier or regressor, wherein the classifier or regressor is configured to classify or regress the second signals to determine a type of the first signals or a magnitude of a continuous physical quantity corresponding to the first signals.

For example, in some embodiments, the first switching circuit comprises a plurality of selectors, and the second switching circuit comprises a plurality of selectors.

For example, in some embodiments, each of the plurality of first selectors is configured to select a corresponding source line of the plurality of source lines under a control of the control circuit to apply a corresponding first signal of the plurality of first signals to the corresponding source line.

For example, in some embodiments, each of the plurality of second selectors is configured to select and activate a corresponding word line of the plurality of word lines under a control of the control circuit to apply a corresponding first signal of the at least one first signal to the memristor unit corresponding to the corresponding word line.

For example, in some embodiments, the output circuit comprises a plurality of current type sensitive amplifiers, and each of the plurality of current type sensitive amplifiers is configured to determine a corresponding second signal of the plurality of second signals based on a reference current and a signal read from a corresponding source line.

At least one embodiment of the present disclosure also provides a signal processing method applicable to a signal processing apparatus, the signal processing apparatus comprising a memristor array, the memristor array comprising a plurality of memristor units and being connected to a plurality of source lines, a plurality of word lines and a plurality of bit lines, each of the plurality of memristor units comprising a memristor, the signal processing method comprising receiving a plurality of first signals on a plurality of channels; selecting at least one source line of the plurality of source lines to apply at least one first signal of the plurality of first signals to the at least one source line respectively by a first switching circuit connected with the plurality of source lines; selecting at least one word line of the plurality of word lines to apply the at least one first signal to the memristor unit corresponding to the at least one word line by a second switching circuit connected with the plurality of word lines; and outputting a plurality of second signals based on conductivity values of memristors of the memristor array.

For example, in some embodiments, the signal processing method may be applied to any of the signal processing devices described above.

For example, in some embodiments, before the at least one first signal is applied, the signal processing method further comprises: in response to a first control signal, selecting the plurality of word lines to apply a first voltage to the memristor units corresponding to the plurality of word lines by the second switching circuit, and select the plurality of bit lines to apply a second voltage to the memristor units corresponding to the plurality of bit lines by a third switching circuit, and applying a ground voltage to the plurality of bit lines.

For example, in some embodiments, applying the at least one first signal to the memristor unit corresponding to the at least one word line comprises in response to a second control signal, selecting and activating each of the at least one word line so as to apply segments of the at least one first signal to the memristor unit corresponding to the at least one word line respectively by the second switching circuit, and applying a ground voltage to the plurality of bit lines.

For example, in some embodiments, a number of the at least one first signal is greater than or equal to 2, wherein selecting the at least one source line of the plurality of source lines to apply the at least one first signal of the plurality of first signals to the at least one source line respectively by the first switching circuit connected with the plurality of source lines comprises controlling the first switching circuit to select the at least one source line of the plurality of source lines to apply each first signal of the at least one first signal to a corresponding source line respectively, and wherein selecting the at least one word line of the plurality of word lines to apply the at least one first signal to the memristor unit corresponding to the at least one word line by the second switching circuit connected with the plurality of word lines comprises controlling the second switching circuit to select and activate the at least one word line of the plurality of word lines to apply each first signal of the at least one first signal to the memristor unit corresponding to a corresponding word line.

For example, in some embodiments, outputting the plurality of second signals based on the conductivity values of the memristors of the memristor array comprises: in response to a third control signal, selecting and activating the at least one word line of the plurality of word lines sequentially by the second switching circuit, so as to output the plurality of second signals through the at least one source line.

For example, in some embodiments, before receiving a plurality of first signals by an input circuit, the method further comprises preprocessing each original signal of a plurality of original signals to form the plurality of first signals with an amplitude within a predetermined range by a preprocessing circuit, and transmitting the plurality of first signals to the input circuit.

For example, in some embodiments, the predetermined range is a resistance-change voltage range or a read voltage range of the memristor.

For example, in some embodiments, the method further comprises classifying or regressing the second signals to determine a type of the first signals or a magnitude of a continuous physical quantity corresponding to the first signals by a classifier or regressor.

BRIEF DESCRIPTION OF THE DRAWINGS

In order to clearly illustrate the technical solution of the embodiments of the disclosure, the drawings of the embodiments will be briefly described in the following; it is obvious that the described drawings are only related to some embodiments of the disclosure and thus are not limitative of the invention

DETAILED DESCRIPTION

Figure 1:
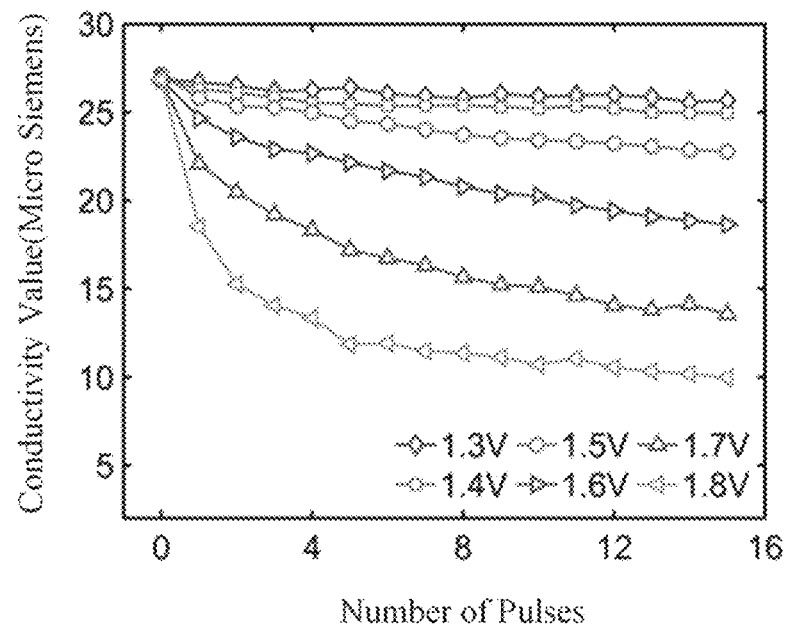
FIG. 1 illustrates a schematic diagram of device characteristics of a memristor according to an exemplary embodiment of the present disclosure.

In order to make objects, technical details and advantages of the embodiments of the disclosure apparent, the technical solutions of the embodiments will be described in a clearly and fully understandable way in connection with the drawings related to the embodiments of the disclosure. It is obvious that the described embodiments are just a part but not all of the embodiments of the disclosure. Based on the described embodiments herein, those skilled in the art can obtain other embodiment(s), without any inventive work, which should be within the scope of the disclosure.

The terms used herein to describe embodiments of the invention are not intended to limit and/or restrict the scope of the invention.

For example, unless otherwise defined, the technical terms or scientific terms used in the present disclosure shall have a general meaning understood by those with general skills in the art to which the present invention belongs.

It should be understood that "first", "second" and similar words used in the present disclosure do not mean any order, quantity or importance, but are only used to distinguish different components. Unless the context clearly indicates otherwise, words such as "one", "a/an" or "the" in the singular form do not mean a quantitative limit, but the existence of at least one.

It should be further understood that the terms "comprising" or "including" and other similar words mean that the elements or objects appearing before the terms cover the elements or objects listed after the terms and their equivalents, and do not exclude other elements or objects. Similar words such as "connection" or "connected" are not limited to physical or mechanical connection, but can comprise electrical connection, whether direct or indirect. "Up", "down", "left" and "right" are only used to represent the relative position relationship. When the absolute position of the described object changes, the relative position relationship may also change accordingly.

Recording the electrical activity of the brain by neural probes has important applications in both the diagnosis of nervous system diseases and the exploration of the working mechanism of the brain. Processing the recorded neuroelectric signals in order to extract useful information is the premise of making good use of them.

In recent years, the number of recording channels of neuroelectric signals has shown a rapid growth trend in the application fields such as brain computer interface, which makes the processing of multi-channel neural signals a major difficulty.

For example, the hardware of multi-channel neural signal processing can use a multiplexer to select the amplified neural signals of each channel in sequence, and then convert them into digital signals by analog-to-digital converter, and then process them in a single digital signal processing unit. However, such a processing method has great limitations in system scalability, computing cost and power consumption.

The memristor changes the conductivity (or resistance) of the device by being applied current or voltage, and then changes its state. The conductivity value is the reciprocal of the resistance value. Specifically, electrical pulse excitation with different amplitude/frequency will cause ion redistribution in the memristor, and then shows different conductivity values. For example, the conductivity value of the memristor may vary with the applied voltage or current. Recently, storage and computing integrated computing system based on memristor has attracted extensive attention. The memristor has the advantages of simple structure, strong scalability, operating at the location of data storage, and low computational power consumption. Therefore, the memristor array may be suitable for the scene of parallel processing of multi-channel neural signals.

Embodiments of the present disclosure provide a signal processing apparatus and a signal processing method. Hereinafter, embodiments of the present disclosure will be described in detail with reference to the accompanying drawings. It should be noted that the same reference numerals in different drawings will be used to refer to the same elements described. FIG. 1 illustrates a schematic diagram of device characteristics of a memristor according to an exemplary embodiment of the present disclosure.

Figure 2A:
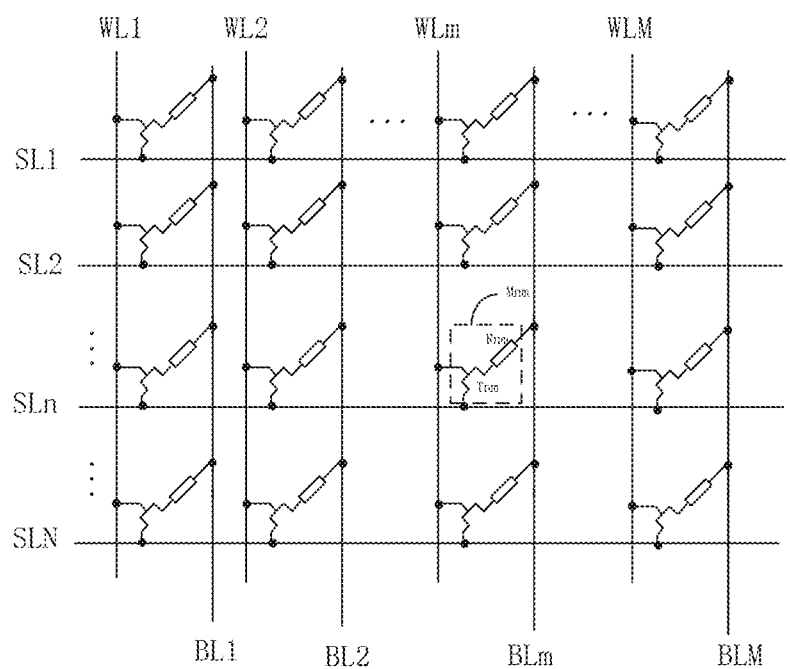
FIG. 2A illustrates a structural diagram of a memristor array according to an exemplary embodiment of the present disclosure.

Referring to FIG. 1, electrical pulses with amplitudes of 1.3 volts (V), 1.4V, 1.5V, 1.6V, 1.7V and 1.8V are applied to the memristor respectively (for example, referring to FIG. 2A, the electrical pulse is applied to the source line terminal, the bit line terminal is grounded, and the word line terminal is applied with 5V voltage). The pulse width of each electrical pulse is 50 nanoseconds (NS). The average results of conductance modulation effects of devices with similar initial conductance states under different voltage conditions may be obtained, in which the diamond connection line represents the results obtained by applying a voltage with an amplitude of 1.3V, the square connection line represents the results obtained by applying a voltage with an amplitude of 1.4V, the circular connection line represents the results obtained by applying a voltage with an amplitude of 1.5V, the right triangle connection line represents the result of applying a voltage with an amplitude of 1.6V, the triangle connection line represents the result of applying a voltage with an amplitude of 1.7V, and the left triangle connection line represents the result of applying a voltage with an amplitude of 1.8V. As may be seen from FIG. 1, when the amplitude of the voltage applied to the memristor is small, the change amplitude of the conductivity value of the memristor is small, while when the amplitude of the voltage applied to the memristor is large, the change amplitude of the conductivity value of the memristor is large. Therefore, the memristor may have a conductivity value stored therein, which varies according to at least one of the voltage and current of the input signal.

Due to this characteristic of memristor, it may be applied to signal processing apparatuses or signal processing methods to process different types of signals.

FIG. 2A illustrates a structural diagram of a memristor array according to an exemplary embodiment of the present disclosure.

Referring to FIG. 2A, a memristor array according to an exemplary embodiment of the present disclosure may be an N*M memristor array, where N and M are integers greater than or equal to 1, for example, N and M are integers greater than or equal to 10, or both are integers greater than or equal to 100. As illustrated in FIG. 2A, the memristor array may comprise N word lines from word lines WL1 to WLN, N bit lines from bit lines BL1 to BLN, M source lines from source lines SL1 to SLM, and N*M memristor units. For example, each of the N*M memristor units may comprise a transistor (T) and a memristor (R), that is, a 1T1R structure, but the embodiments of the present disclosure are not limited thereto. For example, the memristor comprised in the memristor unit is a multi-configurational continuously adjustable memristor. Take the m-th memristor unit Mnm in line n as an example, where n is an integer greater than or equal to 1 and less than or equal to N, and m is an integer greater than or equal to 1 and less than or equal to M. The memristor unit Mnm may comprise a transistor Tnm and a memristor Rnm. For example, the transistor Tnm may be a MOS transistor. For example, the gate of transistor Tnm is connected to word line WLn, the source of transistor Tnm is connected to source line SLn, the drain of transistor Tnm is connected to one end of memristor Rnm, and the other end of memristor Rnm is connected to bit line BLn. The connection between other memristor units and word lines, bit lines and source lines is similar to that of memristor unit Mnm, so it will not be repeated here.

Figure 2B:
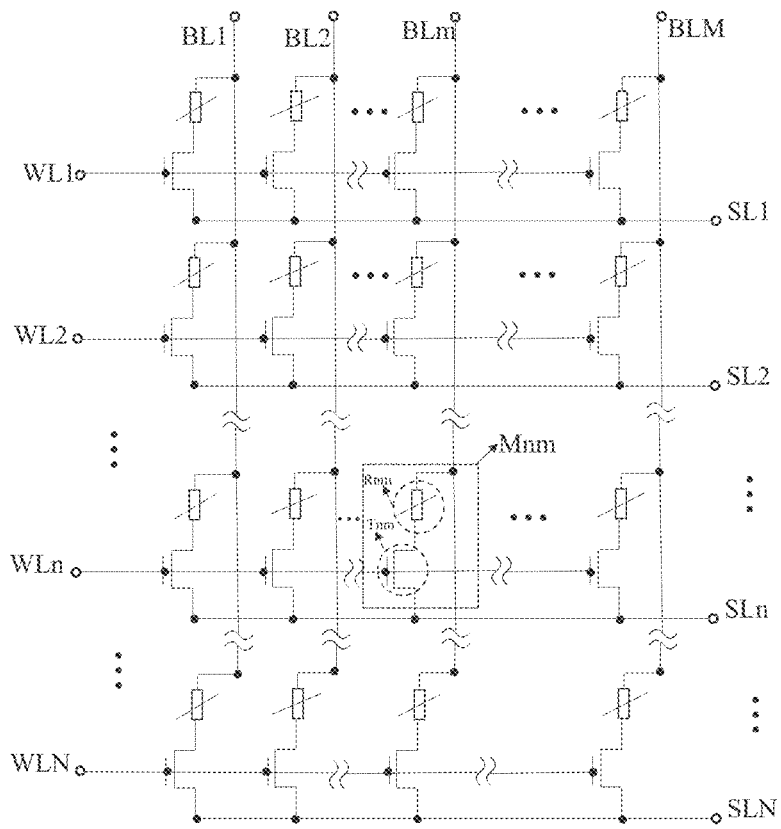
FIG. 2B illustrates a structural diagram of a memristor array according to other exemplary embodiments of the present disclosure.

FIG. 2B illustrates a structural diagram of a memristor array according to other exemplary embodiments of the present disclosure.

Referring to FIG. 2B, a memristor array according to an exemplary embodiment of the present disclosure may be an N*M memristor array, where N and M are integers greater than or equal to 1, for example, N and M are integers greater than or equal to 10, or both are integers greater than or equal to 100. As illustrated in FIG. 2B, the memristor array may comprise N word lines from word line WL1 to WLN, M bit lines from bit line BL1 to BLM, N source lines from source line SL1 to SLN, and N*M memristor units. For example, each of the N*M memristor units may comprise a transistor (T) and a memristor (R), that is, a 1T1R structure, but the embodiments of the present disclosure are not limited thereto. For example, the memristor comprised in the memristor unit is a multi-configurational continuously adjustable memristor. Taking the m-th memristor unit Mnm in line n as an example, where n is an integer greater than or equal to 1 and less than or equal to N, the memristor unit Mnm may comprise a transistor Tnm and a memristor Rnm. For example, the transistor Tnm may be a MOS transistor. For example, the gate of transistor Tnm is connected to word line WLn, the source of transistor Tnm is connected to source line SLn, the drain of transistor Tnm is connected to one end of memristor Rnm, and the other end of memristor Rnm is connected to bit line BLn. The connection between other memristor units and word lines, bit lines and source lines is similar to that of memristor unit Mnm, so it will not be repeated here.

For the convenience of description, an embodiment of the present disclosure will be described below by taking the structure of the memristor illustrated in FIG. 2A as an example. It should be clear to those skilled in the art that the embodiment of the present disclosure may also be applied to the structure of the memristor shown in FIG. 2B.

Figure 3A:
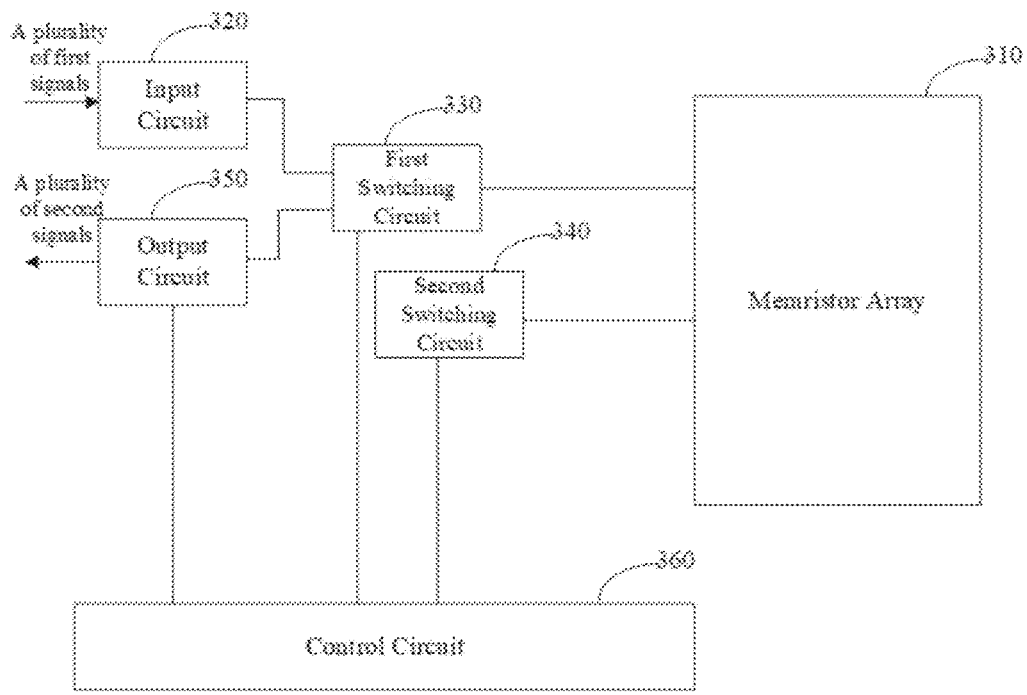
FIG. 3A illustrates a block diagram of a configuration of a signal processing apparatus according to an exemplary embodiment of the present disclosure.
Figure 3B:
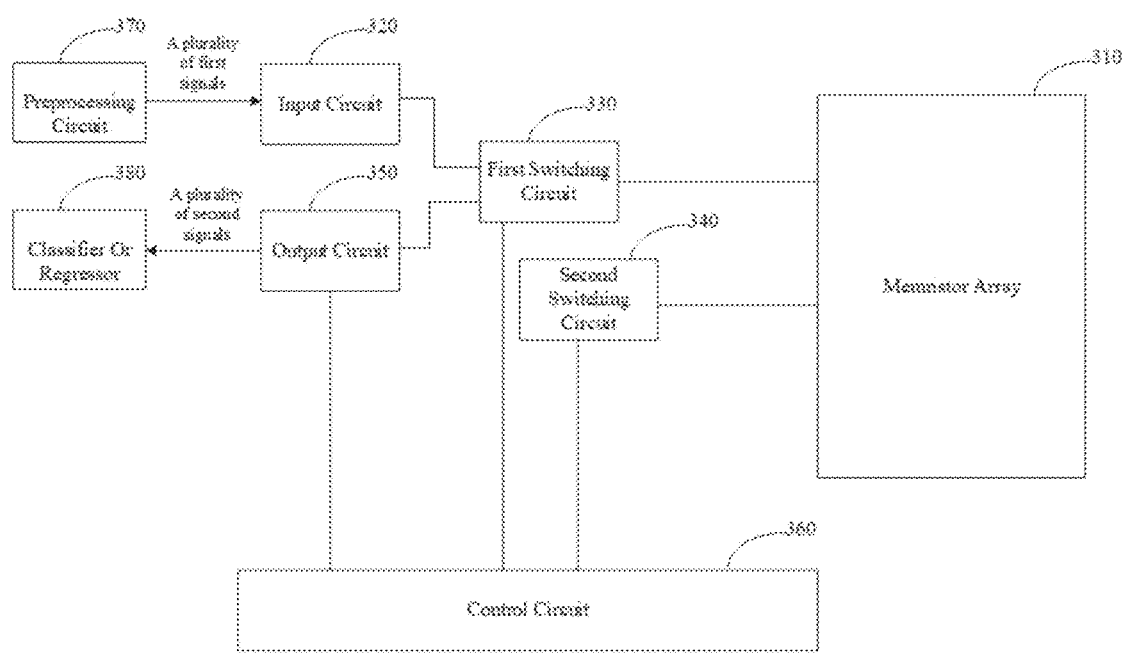
FIG. 3B illustrates a block diagram of a configuration of a signal processing apparatus according to an exemplary embodiment of the present disclosure.

FIGS. 3A and 3B illustrate block diagrams of a structure of a signal processing apparatus according to an exemplary embodiment of the present disclosure.

Referring to FIG. 3A, the signal processing apparatus may comprise a memristor array 310, an input circuit 320, a first switching circuit 330, a second switching circuit 340, an output circuit 350, and a control circuit 360.

In some embodiments, the memristor array 310 may comprise a plurality of memristor units and be connected to a plurality of source lines, a plurality of word lines, and a plurality of bit lines, wherein each of the plurality of memristor units comprises a memristor. For example, the memristor array 310 may adopt the structure of the memristor array in FIG. 2A or FIG. 2B. For the convenience of description, the structure of the memristor array in FIG. 2A will be described below.

In some embodiments, the input circuit 320 may be configured to receive a plurality of first signals on a plurality of channels.

For example, the plurality of first signals on the plurality of channels may be multi-channel signals obtained by the multi-channel signal acquisition device, such as multi-channel neural signals (e. g., multi-channel EEG signals). In addition, the first signal may be a voltage signal.

In some embodiments, the first switch circuit 330 may be connected to the input circuit 320 and may be connected to the plurality of source lines. For example, the first switching circuit 330 may be used to control whether one or more of the plurality of first signals are applied to corresponding source lines in the plurality of source lines.

For example, the first switching circuit 330 may apply a source line voltage to a corresponding source line of the plurality of source lines depending on the operation mode. The source line voltage may comprise a first voltage or a second voltage. The first voltage may be greater than the second voltage. The first voltage may be greater than or equal to 1V and less than or equal to 5V, such as 5V or 4V, for example. The second voltage may comprise, for example, a ground (GND) voltage.

For example, the first switch circuit 330 may turn on the connection with the corresponding source line to input (e. g., apply) the corresponding first signal received by the input circuit 320 to the corresponding source line connected with the first switch circuit 330.

In some examples, the first switching circuit 330 may comprise a plurality of first selectors. Each of the plurality of first selectors may select a corresponding source line of the plurality of source lines to apply a corresponding first signal of the plurality of first signals to the corresponding source line. The configuration of the first switching circuit 330 may refer to the embodiment of FIG. 4.

In some embodiments, the second switch circuit 340 may be connected to the plurality of word lines. For example, the second switching circuit 340 may apply a word line voltage or a ground voltage to a corresponding word line of the plurality of word lines depending on the operation mode.

The word line voltage may comprise a first voltage. The first voltage may comprise, for example, a voltage such as 5V or 4V.

In some examples, the second switch may comprise a plurality of second selectors, each of which may be configured to selectively activate (e. g., turn on) a corresponding word line of the plurality of word lines under the control of the control circuit 360, to apply a corresponding first signal of the at least one first signal to a memristor unit corresponding to the corresponding word line. The configuration of the second switching circuit 340 may refer to the embodiment of FIG. 4.

Figure 4:
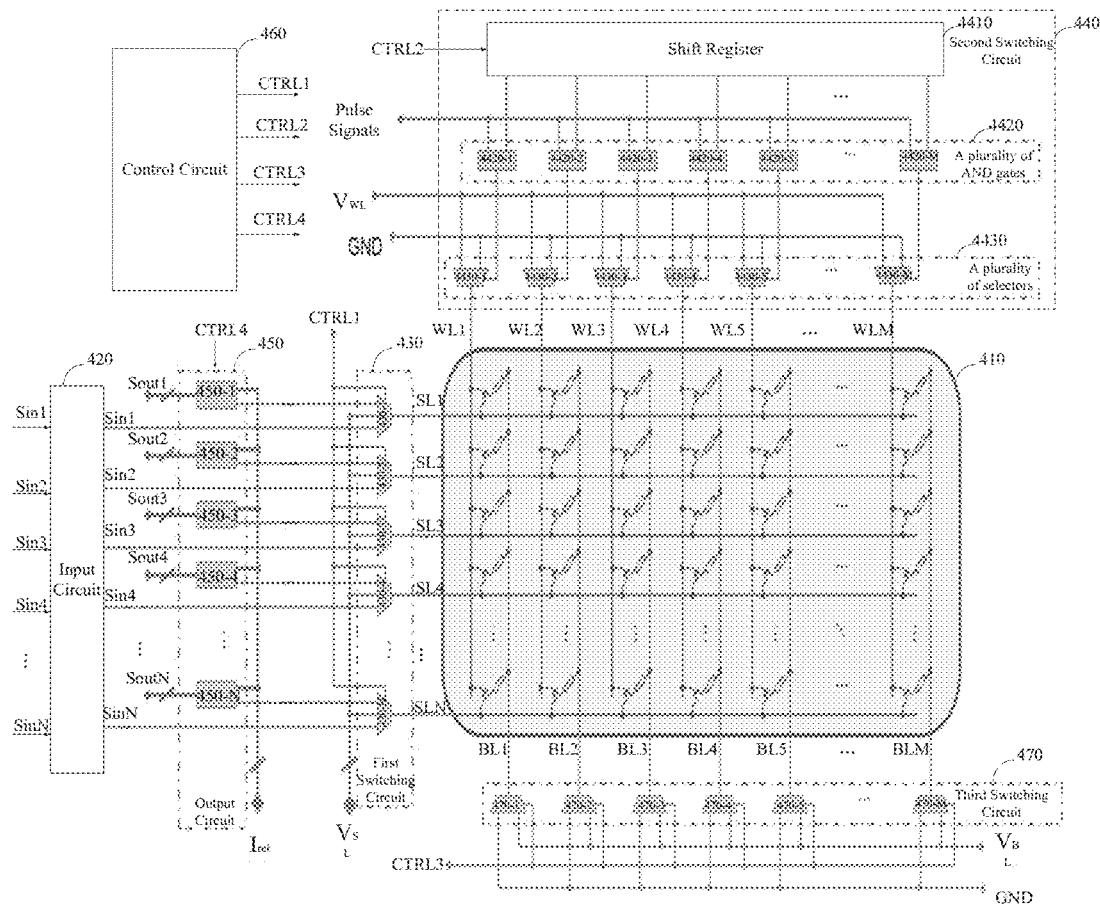
FIG. 4 illustrates a block diagram of a configuration of a signal processing apparatus according to an exemplary embodiment of the present disclosure.

In some embodiments, the signal processing apparatus may also comprise a third switching circuit (e. g., the third switching circuit 470 in FIG. 4). The third switch circuit may be connected with the plurality of bit lines. For example, the third switching circuit may apply a bit line voltage or a ground voltage to a corresponding bit line of the plurality of bit lines depending on the operation mode. The bit line voltage may comprise a first voltage. The first voltage may comprise, for example, a voltage such as 5V or 4V.

In some examples, the third switching circuit may comprise a plurality of third selectors. Each of the plurality of third selectors may be configured to apply a bit line voltage or a ground voltage to a corresponding bit line of the plurality of bit lines under the control of the control circuit 360. The configuration of the third switching circuit may refer to the embodiment of FIG. 4.

In some embodiments, the output circuit 350 is connected to the plurality of source lines. For example, the output circuit 350 may output a plurality of second signals based on the conductivity value of the memristor of the memristor array.

For example, the output circuit 350 may comprise a plurality of current type sensitive amplifiers, each of which may be configured to determine a corresponding second signal of the plurality of second signals based on a reference current and a signal read from a corresponding source line.

In some embodiments, the control circuit 360 may control the operation of one or more of the input circuit 320, the first switching circuit 330, the second switching circuit 340, the third switching circuit, and the output circuit 350.

In some examples, the control circuit 360 may control the operation of one or more of the input circuit 320, the first switching circuit 330, the second switching circuit 340, the third switching circuit and the output circuit 350 in different operation modes (e. g., in response to different mode status signals). For example, the operation mode may comprise a first operation mode (e. g., FORM operation mode), a second operation mode (e. g., PROCESS operation mode), a third operation mode (e. g., READ operation mode), and a fourth operation mode (e. g., SET operation mode). For example, in the FORM or SET operation mode, the memristor array 310 may be initialized so that each memristor in the memristor array 310 reaches the same (or similar) state (e. g., high conductivity state or low resistance state). In the PROCESS operation mode, a plurality of first signals may be applied to the corresponding memristor unit, and after the PROCESS operation mode, the plurality of first signals are encoded into the conductivity value (or resistance value) of the memristor in the memristor unit and stored. In the READ operation mode, the second signal based on the conductivity value of the memristor may be read out. The configuration and operation of the control circuit 360 in various operation modes will then be described in combination with FIGS. 6A, 6B and 6C.

It should be noted that although the present disclosure describes that the control circuit 360 may control the operation of one or more of the input circuit 320, the first switching circuit 330, the second switching circuit 340, the third switching circuit and the output circuit 350, the embodiments of the present disclosure are not limited thereto. For example, the control circuit 360 may be implemented as separated controllers, each of which controls a corresponding one of the input circuit 320, the first switching circuit 330, the second switching circuit 340, the third switching circuit and the output circuit 350, respectively.

In some embodiments, the control circuit 360 may be configured to control the first switch circuit 330 to select at least one source line of the plurality of source lines to apply at least one first signal of the plurality of first signals to the at least one source line respectively; controlling the second switch circuit 340 to selectively activate at least one of the plurality of word lines to apply the at least one first signal to the memristor unit corresponding to the at least one word line; and controlling the output circuit 350 to output a plurality of second signals based on the conductivity value of the memristor of the memristor array 310.

In some embodiments, before the at least one first signal is applied, in a first operation mode (e. g., FORM operation mode) or a fourth operation mode (SET operation mode), the control circuit 360 may be configured to control the second switching circuit 340 to select the plurality of word lines to apply a first voltage to the memristor unit corresponding to the plurality of word lines; and controlling a third switching circuit to select the plurality of bit lines to apply a second voltage to the memristor unit corresponding to the plurality of bit lines. For example, the first voltage may comprise a voltage such as 5V, and the second voltage may comprise a ground (GND) voltage.

In some embodiments, in the second operation mode (e. g., PROCESS operation mode), the control circuit 360 is also configured to control the second switch circuit 340 to select and activate each of the at least one word line in sequence to apply segments of the at least one first signal to the memristor unit corresponding to the at least one word line, respectively.

In some embodiments, in the third operation mode (e. g., READ operation mode), the control circuit 360 is also configured to control the second switch circuit 340 to select and activate at least one of the plurality of word lines in sequence so that the output circuit 350 outputs the plurality of second signals through the at least one source line.

Referring to FIG. 3B, in some embodiments, the signal processing apparatus may also comprise a preprocessing circuit 370 configured to preprocess each of the plurality of original signals to form the plurality of first signals with an amplitude within a predetermined range and transmit the plurality of first signals to the input circuit 320.

For example, the predetermined range may be a resistance-change voltage range or a read voltage range of the memristor. For example, the resistance-change voltage range of the memristor may be 0.8~2V, and the read voltage range of the memristor may be 0.1~0.5V.

In some examples, the preprocessing circuit 370 may comprise an amplification circuit and a bias circuit. For example, the bias circuit may be configured to provide a bias signal, and the amplification circuit may be configured to process the original signal based on the bias signal to form the plurality of first signals with an amplitude within the predetermined range.

For example, the plurality of original signals may be multi-channel signals obtained by a multi-channel signal acquisition device, such as multi-channel neural signals. In one example, multi-channel signals (i.e., multi-channel neural signals) may be collected from the brain by using a multi-channel signal acquisition device.

Referring to FIG. 3B, in some embodiments, the signal processing apparatus may also comprise a classifier or regressor 380, wherein the classifier or regressor 380 is configured to classify the second signal to determine the type of the first signal.

For example, the classifier or regressor 380 may comprise a machine learning classifier or regressor. For example, the classifier or regressor 380 may also be configured to classify or regress the second signal output by the output circuit 350 by using a traditional machine learning method to obtain the type of the first signal or the magnitude of the continuous physical quantity corresponding to the first signal. For example, machine learning classification or regression methods may comprise linear discriminant analysis (LDA) methods, decision tree methods, random forest (RF) methods, etc. Since the second signal is based on the memristor conductance distribution of the memristor array 310, the second signal may be easily classified or regressed by the classifier or regressor 380. Further, by classifying or regressing the second signal, the type of the first signal or the magnitude of the continuous physical quantity corresponding to the first signal may be obtained.

For example, the classifier or regressor 380 may comprise a neural network classifier or regressor. For example, the classifier or regressor 380 may also be configured to classify or regress the second signal output by the output circuit 350 by using a neural network classification method to obtain the type of the first signal or the magnitude of the continuous physical quantity corresponding to the first signal. For example, neural network classification or regression methods may comprise BP (back propagation) neural network method, RBF (radial basis function) neural network method, convolution neural network method, etc. Since the second signal is based on the memristor conductance distribution of the memristor array 310, the second signal may be easily classified or regressed by the classifier or regressor 380. Further, by classifying or regressing the second signal, the type of the first signal or the magnitude of the continuous physical quantity corresponding to the first signal may be obtained.

For example, the classifier or regressor 380 may be implemented by at least one of ASIC (application specific integrated circuit), FPGA (field programmable gate array), GPU (graphics processing unit) and CPU (central processing unit), alternatively, the classifier may be implemented by hardware, firmware or software and any combination thereof. Moreover, these classifiers are trained with a large number of training sample sets, which comprise historical data obtained in different situations. After training to a certain extent, the classifier may classify the input new second signal.

In the embodiment of the present disclosure, since the memristor has small volume, low power consumption and easy high-density integration, the signal processing device according to the embodiment of the present disclosure has the advantages of small volume, low power consumption and easy integration. In addition, the memristor array converts the multi-channel first signal as an analog signal into a second signal based on the resistance value of the memristor for further processing (e. g., classification) without additional analog-to-digital conversion components to process the first signal. Therefore, the signal processing apparatus according to the embodiment of the present disclosure further reduces the volume and reduces the cost.

It should be noted that the signal processing apparatus according to the embodiment of the present disclosure described above is only an exemplary structure. However, the present disclosure is not limited thereto. For example, some of these components may be omitted or additional components may be added.

FIG. 4 illustrates a block diagram of a structure of a signal processing apparatus according to an exemplary embodiment of the present disclosure.

Referring to FIG. 4, the signal processing apparatus may comprise a memristor array 410, an input circuit 420, a first switching circuit 430, a second switching circuit 440, an output circuit 450, and a control circuit 460.

For example, the configurations of the memristor array 410, the input circuit 420, the first switching circuit 430, the second switching circuit 440, the output circuit 450, and the control circuit 460 may be the same or similar to the configurations of the memristor array 310, the input circuit 320, the first switching circuit 330, the second switching circuit 340, the output circuit 350, and the control circuit 360 in the signal processing apparatus in FIG. 3A, respectively.

In some embodiments, the memristor array 410 may comprise a plurality of memristor units and be connected to a plurality of source lines, a plurality of word lines, and a plurality of bit lines, wherein each of the plurality of memristor units comprises a memristor. For example, the memristor array 410 may adopt the structure of the memristor array in FIG. 2A or FIG. 2B. Referring to FIG. 4, the memristor array 410 may be a memristor array of size N*M, where N and M are integers greater than or equal to 1, for example, N and M are integers greater than or equal to 10, or both are integers greater than or equal to 100. As illustrated in FIG. 4, the memristor array 410 may comprise N word lines from word lines WL1 to WLN, N bit lines from bit lines BL1 to BLN, M source lines from source lines SL1 to SLM, and N*M memristor units. For example, each of the N*M memristor units may comprise a transistor (T) and a memristor (R), i.e., a 1T1R structure. However, embodiments of the present disclosure are not limited to this, and any suitable memristor unit structure may be adopted.

In some embodiments, referring to FIG. 4, the input circuit 420 may be configured to receive N first signals on the plurality of channels, the first signals Sin1 to SinN. That is, the number of channels of the first signal may be N. It should be understood that although the number of first signals (i.e., the number of channels) is described as the same as the number of rows of the memristor array, embodiments of the present disclosure are not limited to this, and the number of first signals may be greater than or less than the number of rows of the memristor array.

For example, the first signals Sin1 to SinN may be multi-channel signals obtained by a multi-channel signal acquisition device, such as multi-channel neural signals (e. g., multi-channel brain electrical signals). In addition, the first signals Sin1 to SinN may be voltage signals.

In some embodiments, the first switch circuit 430 may be connected to the input circuit 420 and may be connected to a plurality of source lines SL1 to SLN. For example, the first switching circuit 430 may be used to control whether one or more of the plurality of first signals are applied to the corresponding source lines in the source lines SL1 to SLN.

Figure 5A:
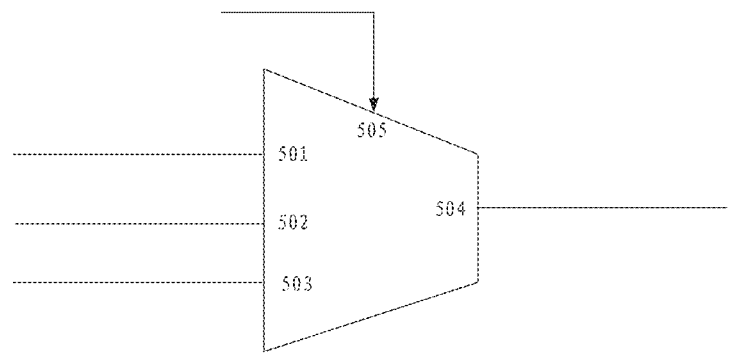
FIGS. 5A and 5B illustrate structural diagrams of selectors according to an embodiment of the present disclosure.
Figure 5B:
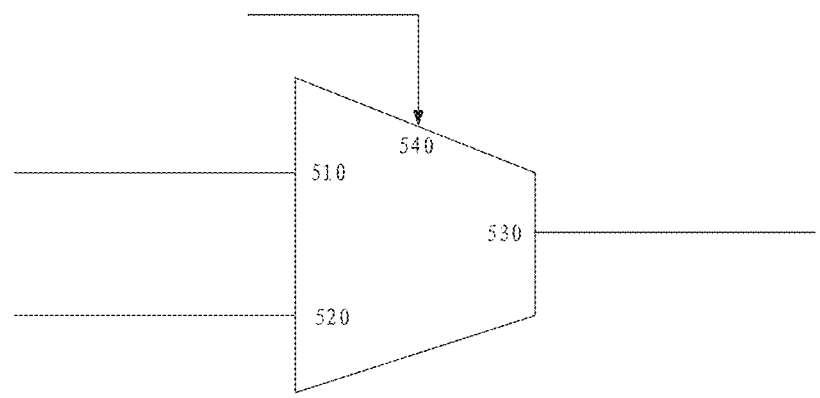

Referring to FIG. 4, the first switch circuit 430 may comprise a plurality of first selectors (e. g., N first selectors 430-1 to 430-N). It should be understood that although the number of first selectors is described as the same as the number of rows of memristor array 410, embodiments of the present disclosure are not limited to this, and the number of first selectors may be greater than or less than the number of rows of memristor array 410. FIGS. 5A and 5B illustrate a configuration diagram of a selector according to an embodiment of the present disclosure.

Referring to FIG. 5A, the selector may comprise a first input terminal 501, a second input terminal 502, a third input terminal 503, an output terminal 504, and a control terminal 505. When the control terminal 505 is activated, one of the first input terminal 501, the second input terminal 502 and the third input terminal 503 may be connected to the output terminal 504.

Referring to FIG. 5B, the selector may comprise a first input terminal 510, a second input terminal 520, an output terminal 530, and a control terminal 540. When the control terminal 540 is activated, one of the first input terminal 510 and the second input terminal 520 may be connected to the output terminal 530.

In some embodiments, the configuration of FIG. 5A may be applied to each of the first selectors 430-1 to 430-N. In the following description, it is assumed that each of the first selectors 430-1 to 430-N adopts the structure of FIG. 5A.

Continuing to refer to FIG. 4, each of the N first selectors 430-1 to 430-N may be connected to a corresponding channel of the input circuit 420, respectively. For example, the first signal Sin1 may be connected to the third input terminal of the first selector 430-1, the first signal Sin2 may be connected to the third input terminal of the first selector 430-2, and the first signal SinN may be connected to the third input terminal of the first selector 430-N.

Continuing to refer to FIG. 4, each of the N first selectors 430-1 to 430-N may be connected to the corresponding source line respectively. For example, the output terminal of the first selector 430-1 is connected to the source line SL1, the output terminal of the second selector 430-2 is connected to the source line SL2, and the output terminal of the first selector 430-N is connected to the source line SLN.

In some examples, each of the first selectors 430-1 to 430-N may select a corresponding source line in the source lines SL1 to SLN to apply a corresponding first signal in the first signals Sin1 to SinN to the corresponding source line.

For example, under the control of the control circuit 460 (e. g., in response to the first control signal CTRL1), the first selectors 430-1 to 430-N may turn on the connection with the corresponding source line depending on the operation mode to input (e. g., apply) the corresponding first signal received by the input circuit 420 to the corresponding source line connected with the first selectors 430-1 to 430-N.

In some examples, the first selectors 430-1 to 430-N may apply the source line voltage $V_{SL}$ to the corresponding source lines in the source lines SL1 to SLN depending on the operation mode. The source line voltage $V_{SL}$ may comprise a first voltage. The first voltage may comprise, for example, a voltage such as 5V or 4V.

For example, under the control of the control circuit 460 (e. g., in response to the first control signal CTRL1), the first selectors 430-1 to 430-N may turn on the connection between the second input terminal of each of the first selectors 430-1 to 430-N and the corresponding source line depending on the operation mode, wherein the second input terminal is input the source line voltage $V_{SL}$.

In some embodiments, the second switch circuit 440 may be connected to the word lines WL1 to WLM.

Referring to FIG. 4, the second switch circuit 440 may comprise a plurality of second selectors (e. g., M second selectors 440-1 to 440-M) and a signal generation circuit. It should be understood that although the number of second selectors is described as the same as the number of columns of the memristor array 410, embodiments of the present disclosure are not limited to this, and the number of second selectors may be greater than or less than the number of columns of the memristor array 410.

In some embodiments, the configuration of FIG. 5B may be applied to each of the second selectors 440-1 to 440-M. In the following description, it is assumed that each of the second selectors 440-1 to 440-N adopts the structure of FIG. 5B.

Referring to FIG. 4, the first input terminal of each of the second selectors 440-1 to 440-N may be input with a ground voltage, the second input terminal of each of the second selectors 440-1 to 440-N may be input with a word line voltage $V_{WL}$, and the output terminal of each of the second selectors 440-1 to 440-N may be connected to a corresponding word line in the word lines WL1 to WLM.

In some embodiments, the signal generation circuit is configured to generate a control signal for controlling each of the second selectors 440-1 to 440-M. For example, the signal generation circuit may comprise a shift register 4410 and a plurality of AND gates 4420 (AND gates 4420-1 to 4420-M). However, embodiments of the present disclosure are not limited thereto. For example, other suitable signal generation circuits, such as an M-sequence generator, may be used to generate a control signal for controlling each of the second selectors 440-1 to 440-M.

Referring to FIG. 4, each of the plurality of output terminals (e. g., M output terminals) of the shift register 4410 is connected to one input terminal of a corresponding one of the plurality of AND gates 4420, and the other input terminal of the corresponding one of the plurality of AND gates 4420 is connected with a pulse signal to the other input of the selector, and the output terminal of the corresponding one of the plurality of AND gates 4420 is connected to the control terminal of the corresponding second selector.

In some examples, each of the second selectors 440-1 to 440-M may apply the word line voltage $V_{WL}$ to the corresponding word lines in the word lines WL1 to WLM depending on the operation mode to activate the corresponding word lines. The word line voltage $V_{WL}$ may comprise a first voltage. The first voltage may comprise, for example, a voltage such as 5V or 4V.

For example, under the control of the control circuit 460 (e. g., in response to the second control signal CTRL2), the signal generation circuit may generate a control signal to control each of the second selectors 440-1 to 440-M to apply the word line voltage $V_{WL}$ to the corresponding word lines in the word lines WL1 to WLM.

In some embodiments, the signal processing apparatus may also comprises a third switching circuit 470. The third switch circuit 470 may be connected to the bit lines BL1 to BLM.

Referring to FIG. 4, the third switch circuit 470 may comprise a plurality of third selectors (e. g., M third selectors 470-1 to 470-M). It should be understood that although the number of third selectors is described as the same as the number of columns of the memristor array 410, embodiments of the present disclosure are not limited to this, and the number of third selectors may be greater than or less than the number of columns of the memristor array 410.

In some embodiments, the configuration of FIG. 5B may be applied to each of the third selectors 470-1 to 470-M. In the following description, it is assumed that each of the third selectors 470-1 to 470-M adopts the structure of FIG. 5B.

Referring to FIG. 4, the first input terminal of each of the third selectors 470-1 to 470-M may be input with a ground voltage, the second input terminal of each of the third selectors 470-1 to 470-M may be input with a bit line voltage $V_{BL}$, and the output terminal of each of the second selectors 440-1 to 440-N may be connected to the corresponding bit lines BL1 to BLM.

For example, each of the third selectors 470-1 to 470-M may apply a bit line voltage $V_{BL}$ or a ground voltage to the corresponding bit lines in the bit lines BL1 to BLM depending on the operation mode. The bit line voltage may comprise a first voltage. The first voltage may comprise, for example, a voltage such as 5V or 4V.

In some examples, each of the third selectors 470-1 to 470-M may be configured to select the corresponding bit lines of the bit lines BL1 to BLM to apply the bit line voltage $V_{BL}$ or ground voltage to the corresponding bit lines under the control of the control circuit 460 (e. g., in response to the third control signal CTRL3).

In some embodiments, the output circuit 450 is connected to the source lines SL1 to SLN. For example, the output circuit 450 may output N second signals Sout1 to SoutN based on the resistance value of the memristor of the memristor array 410.

In some examples, the output circuit 450 may comprise a plurality of current type sense amplifiers 450-1 to 450-N, each of which may determine the corresponding second signal in the second signals Sout1 to SoutN based on the reference current Iref and the signal read from the corresponding source line (e.g., through the corresponding selector) and under the control of the control circuit 460 (e. g., in response to the fourth control signal CTRL4). For example, each of the current type sensitive amplifiers 450-1 to 450-N may read a signal from the source line (e. g., by generating a read voltage and sensing the current of the corresponding source line at the read voltage), and the read signal read from the source line may be compared with the reference current Iref to determine the quantized read signal as the second signals Sout1 to SoutN. However, embodiments of the present disclosure are not limited to this, and any suitable output (or readout) circuit may be used. For example, other devices such as transconductance amplifiers and mode converters may be used to determine the quantized read signal from the signal read from the source line as the second signals Sout1 to SoutN. In this case, an appropriate bit line voltage $V_{BL}$ may be applied to the bit lines BL1 to BLM as the read voltage.

In some embodiments, the control circuit 460 may control the operation of one or more of the input circuit 420, the first switching circuit 430, the second switching circuit 440, the third switching circuit, and the output circuit 450.

In some examples, the control circuit 460 may control the operation of one or more of the input circuit 420, the first switching circuit 430, the second switching circuit 440, the third switching circuit 470, and the output circuit 450 in different operation modes (e. g., in response to different mode status signals). For example, the operation mode may comprise a first operation mode (e. g., FORM operation mode), a second operation mode (e. g., PROCESS operation mode), a third operation mode (e. g., READ operation mode), and a fourth operation mode (e. g., SET operation mode). For example, in the FORM or SET operation mode, the memristor array 410 may be initialized so that each memristor in the memristor array 410 reaches the same (or similar) state (e. g., high conductivity state or low resistance state). In the PROCESS operation mode, the first signals Sin1 to SinN may be applied to the corresponding memristor unit, and after the PROCESS operation mode, the first signals Sin1 to SinN are encoded into the conductivity value (or resistance value) of the memristor in the memristor unit and stored. In the READ operation mode, a second signal based on the resistance value of the memristor may be read out. The configuration and operation of the control circuit 460 in various operation modes will then be described in connection with FIGS. 6A, 6B and 6C.

It should be noted that although the present disclosure describes that the control circuit 460 may control the operation of one or more of the input circuit 420, the first switching circuit 430, the second switching circuit 440, the third switching circuit 470 and the output circuit 450, the embodiments of the present disclosure are not limited thereto. For example, the control circuit 460 may be implemented as separate controllers, each of which controls a corresponding one of the input circuit 420, the first switching circuit 430, the second switching circuit 440, the third switching circuit 470 and the output circuit 450, respectively.

In some embodiments, the control circuit 460 may be configured to control the first switch circuit 430 to select at least one of the source lines SL1 to SLN to apply at least one of the first signals Sin1 to SinN to the at least one source line, respectively; control the second switch circuit 440 to select and activate at least one of the word lines WL1 to WLM to apply the at least one first signal to the memristor unit corresponding to the at least one word line; and control the output circuit 450 to output a plurality of second signals based on the resistance values of the memristors of the memristor array 410. For example, when the first signals Sin1 to SinN are applied to the source lines SL1 to SLN respectively, the output second signals are the second signals Sout1 to SoutN.

In some embodiments, before the at least one first signal is applied, in a first operation mode (e. g., FORM operation mode) or a fourth operation mode (SET operation mode), the control circuit 460 may be configured to control the second switching circuit 440 to select the word lines WL1 to WLM to apply the first voltage to the memristor units corresponding to the word lines WL1 to WLM; and control the third switch circuit to select the bit lines BL1 to BLM to apply the second voltage to the memristor units corresponding to the bit lines BL1 to BLM. For example, the first voltage may comprise a voltage such as a 5V voltage, and the second voltage may comprise a ground (GND) voltage.

In some embodiments, in the second operation mode (e. g., PROCESS operation mode), the control circuit 460 is also configured to control the second switch circuit 440 to successively select and activate each of the at least one word line to apply segments of the at least one first signal to the memristor unit corresponding to the at least one word line, respectively.

In some embodiments, in the third operation mode (e. g., READ operation mode), the control circuit 460 is further configured to control the second switch circuit 440 to select and activate the word lines WL1 to WLM in sequence, so that the output circuit 450 outputs a plurality of second signals Sout1 to SoutN through the source lines SL1 to SLN.

A schematic diagram of the operation of the signal processing apparatus in FIG. 4 under various operation modes will be described below in connection with FIGS. 6A-6C.

Figure 6A:
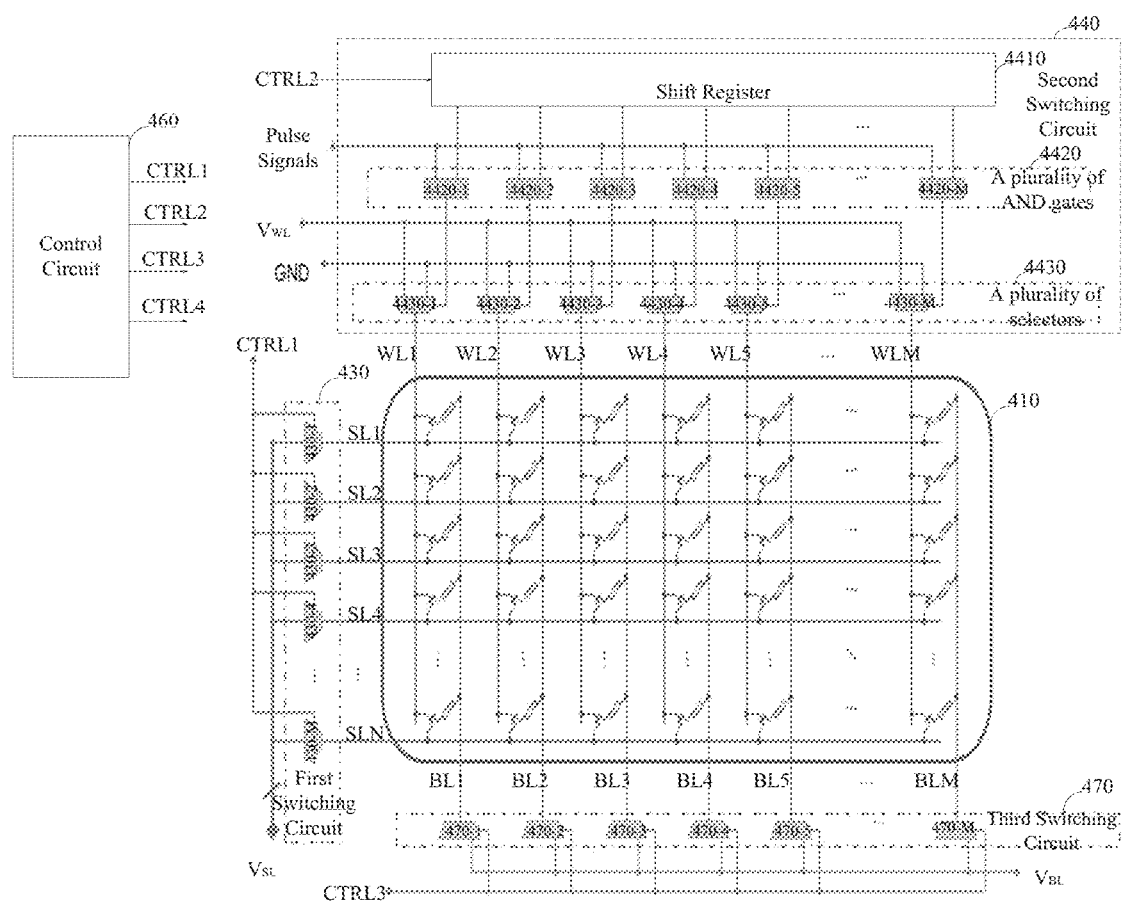
FIG. 6A illustrates a schematic diagram of the operation of a signal processing apparatus in a first operation mode (e. g., FORM operation mode) or a fourth operation mode (SET operation mode) according to an embodiment of the present disclosure.

FIG. 6A illustrates a schematic diagram of the operation of a signal processing apparatus in a first operation mode (e. g., FORM operation mode) or a fourth operation mode (SET operation mode) according to an embodiment of the present disclosure. The operation of the signal processing apparatus in the FORM operation mode or the SET operation mode will be described below with reference to FIGS. 4 and 6A.

In the FORM operation mode, the memristor array 410 is electrically initialized (referred to as FORM operation). After initialization, the memristor in the memristor array 410 may be switched between the high conductivity state and the low conductivity state. For example, the FORM operation may be performed before the first signals Sin1 to SinN are applied. For example, in the FORM operation mode, the bit line voltage may be 3-5V; the source line voltage may be a ground voltage (e. g., 0V); the word line voltage may be 1-3V.

In the SET operation mode, the memristor array 410 is set (referred to as SET operation). Through the set operation, the memristor in the memristor array 410 changes from a low conductivity state to a high conductivity state. For example, in the SET operation mode, the bit line voltage may be 1-3V; the source line voltage may be a ground voltage (e. g., 0V); the word line voltage may be 1-3V.

In the embodiment of the present disclosure, the first switching circuit 430, the second switching circuit 440 and the third switching circuit 470 are controlled by the control circuit 460 to select the memristor unit requiring FORM operation or SET operation in the memristor array 410. For example, after the memristor unit is applied with the appropriate source line voltage $V_{SL}$, word line voltage $V_{WL}$ and bit line voltage $V_{BL}$, the memristor unit is activated to perform the corresponding operation (e. g., FORM operation or SET operation).

In the embodiment of the present disclosure, the source line voltage $V_{SL}$ may be applied to at least one of the source lines SL1 to SLN respectively through the first switching circuit 430. The source line voltage $V_{SL}$ may comprise a first voltage. The first voltage may be greater than or equal to 1V and less than or equal to 5V, such as 5V or 4V, for example.

For example, under the control of the control circuit 460, in response to the first control signal CTRL1, each of the first selectors 430-1 to 430-M connects the second input terminal, to which the source line voltage $V_{SL}$ is applied, to the output terminal to apply the source line voltage $V_{SL}$ to the corresponding source lines in the source lines SL1 to SLN.

In the embodiment of the present disclosure, the word line voltage $V_{WL}$ may be applied to the word lines WL1 to WLM respectively through the second switching circuit 440. The word line voltage $V_{WL}$ may comprise a first voltage. The first voltage may be greater than or equal to 1V and less than or equal to 5V, such as 5V or 4V, for example.

For example, under the control of the control circuit 460, a control signal controlling each of the plurality of selectors 4430 is generated by a signal generation circuit comprising a shift register 4410 and a plurality of AND gates 4420 in response to the second control signal CTRL2. Based on the generated control signal, each of the selectors 4430-1 to 4430-M connects the first input terminal, to which the word line voltage $V_{WL}$ is applied, to the corresponding word line in the word lines WL1 to WLM.

In the embodiment of the present disclosure, the bit line voltage $V_{BL}$ may be applied to the bit lines BL1 to BLM respectively through the third switching circuit 470. The bit line voltage $V_{BL}$ may comprise a first voltage. The first voltage may be greater than or equal to 1V and less than or equal to 5V, such as 5V or 4V, for example.

For example, under the control of the control circuit 460, in response to the third control signal CTRL3, each of the first selectors 430-1 to 430-M connects the second input terminal, to which the bit line voltage $V_{BL}$ is applied, to the output terminal to apply the bit line voltage $V_{BL}$ to the corresponding bit lines in the bit lines BL1 to BLM.

After the operation of FORM operation mode or SET operation mode, the memristors in the memristor array may be in a similar high conductivity state.

Figure 6B:
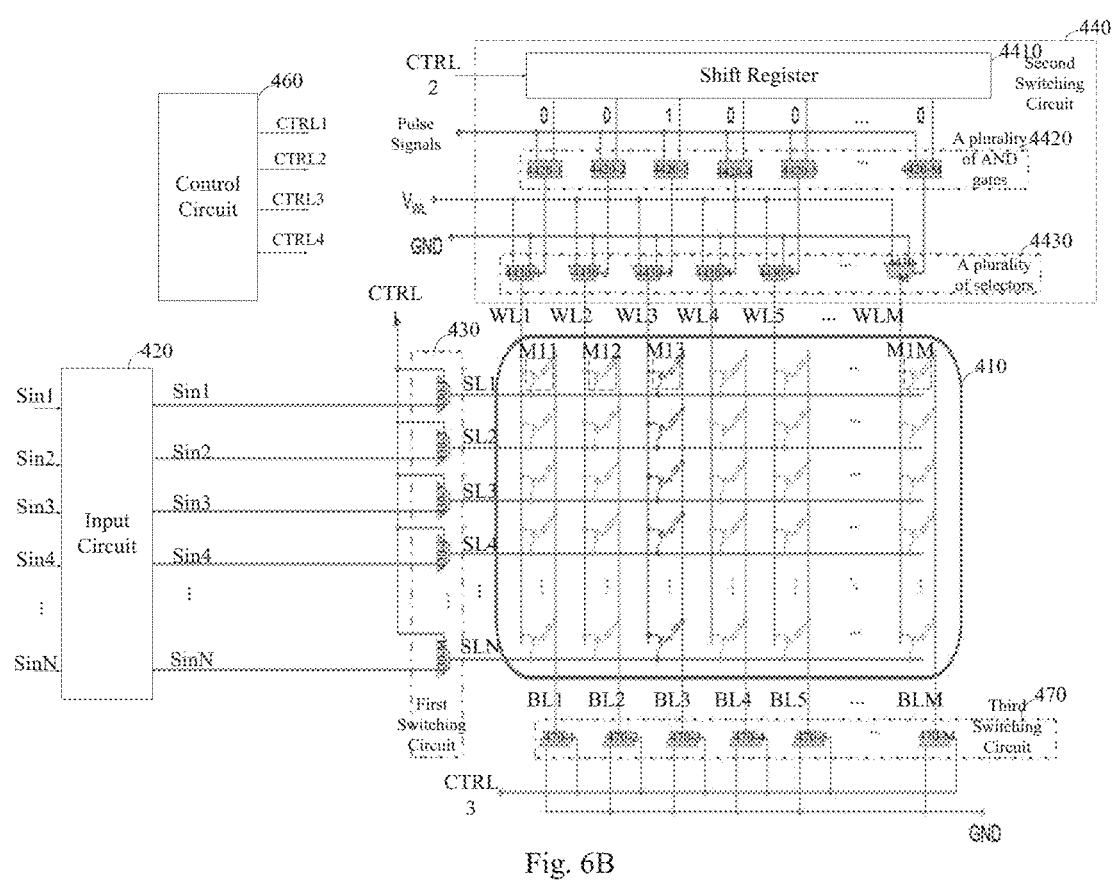
FIG. 6B illustrates a schematic diagram of the operation of a signal processing apparatus in a second operation mode (e. g., a PROCESS operation mode) according to an embodiment of the present disclosure.

FIG. 6B illustrates a schematic diagram of the operation of a signal processing apparatus in a second operation mode (e. g., a PROCESS operation mode) according to an embodiment of the present disclosure.

In the PROCESS operation mode, the first signals Sin1 to SinN are respectively applied (e. g., written) to the corresponding memristor units of the memristor array 410, thereby modulating the conductivity of the memristors in the memristor units. For example, by applying the first signals Sin1 to SinN, the memristors in the memristor units are reset (RESET).

In some embodiments, for each of the first signals Sin1 to SinN, each first signal segment may be applied to a memristor unit corresponding to the source line to which the first signal is applied.

In an embodiment of the present disclosure, WL1 to WLN may be activated (e. g., turned on) sequentially (e. g., column by column) by the second switching circuit 440 to apply a word line voltage (e. g., 5V) to the corresponding word line, and a ground voltage may be applied to the corresponding bit line by the third switching circuit 470 to sequentially activate the memristor units of the corresponding column. In this case, a segment of each first signal may be applied to the corresponding memristor unit.

In some examples, in the PROCESS operation mode, the shift register 4410 may output cyclically shifted data. For example, at the first time, the shift register 4410 may output "1000 . . . 000", at the second time, the shift register may output "0100 . . . 000", at the third time (the time corresponding to FIG. 6B), the shift register may output "0010 . . . 000", and at the M time, the shift register may output "0000 . . . 001". At each time, the shift register 4410 generates a data signal so that one of the plurality of selectors 4430 is selected. It is assumed that the first signal Sin1 may be divided into K data segments (the first data segment to the K data segment), and K may be greater than or equal to 1 and less than or equal to M. For the convenience of description, it is further assumed that M is greater than 3 and K is equal to M. In this case, at the first time, the word line voltage $V_{WL}$ is applied to the word line WL1, thereby activating the word line WL1 and the first column of memristor units, and the first data segment of the first signal Sin1 is applied to the memristor unit M11. At the second time, the word line voltage $V_{WL}$ is applied to the word line WL2, thereby activating the word line WL2 and the second column of memristor units, and the second data segment of the first signal Sin1 is applied to the memristor unit M12. At the third time, the word line voltage $V_{WL}$ is applied to the word line WL3, thereby activating the word line WL3 and the third column of memristor units, and the third data segment of the first signal Sin1 is applied to the memristor unit M13. Similarly, at the M-th time, the word line voltage is applied to the word line WLM to activate the word line WLM and the M-th column of memristor units, and the K-th data segment of the first signal Sin1 is applied to the memristor unit M1M. Thus, the segments of the first signal Sin1 are sequentially applied to the memristor units M11 to M1M, respectively.

After the PROCESS operation mode, the first signal is encoded into the conductivity value (or resistance value) of the memristor in the memristor unit and stored as a result of the processing of the first signals Sin1 to SinN by the memristor array 410. In the embodiment of the present disclosure, the memristor array 410 encodes, compresses and retains the information of the first signal. Therefore, a second signal reflecting the characteristics (e. g., type) of the first signal may be output from the memristor array 410.

Figure 6C:
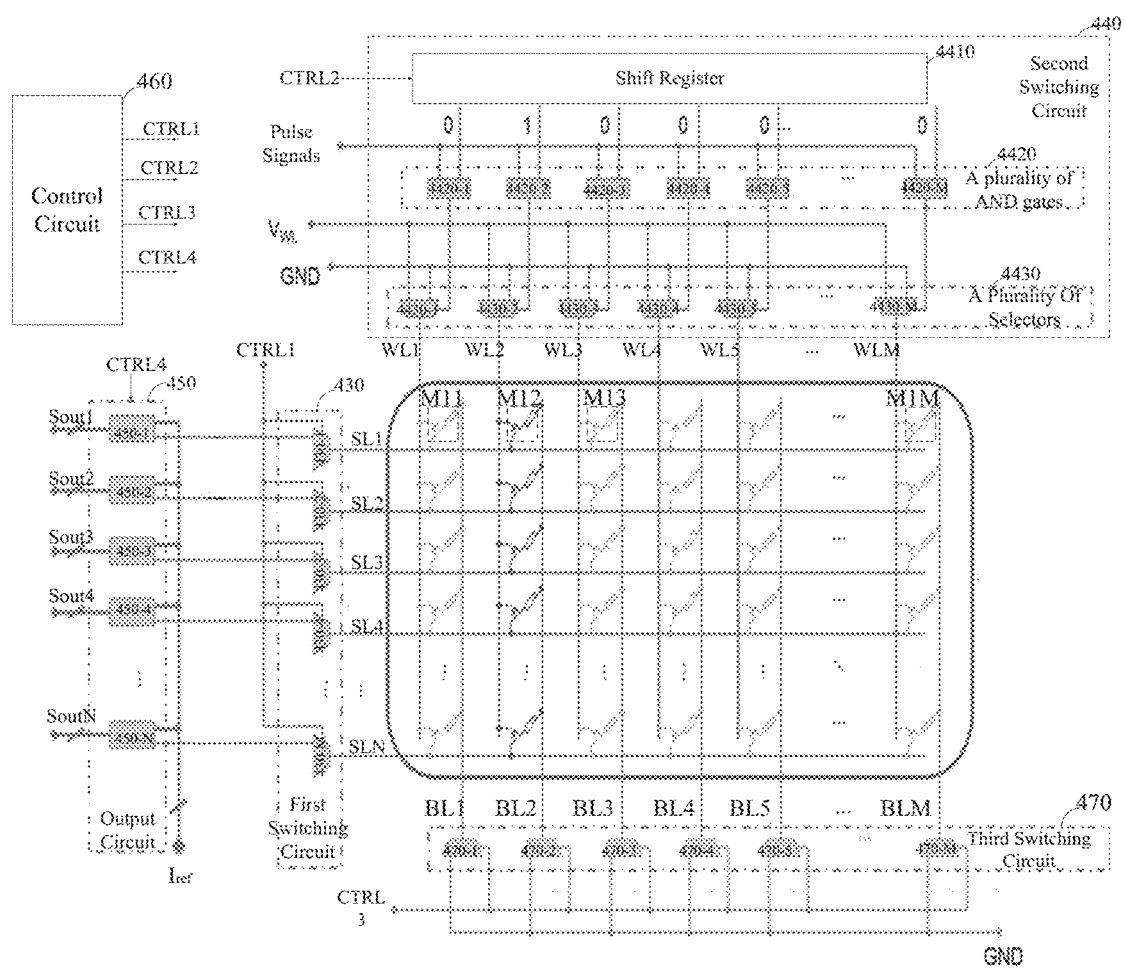
FIG. 6C illustrates a schematic diagram of the operation of a signal processing apparatus in a third operation mode (e.g., a READ operation mode) according to an embodiment of the present disclosure.

FIG. 6C illustrates a schematic diagram of the operation of a signal processing apparatus in a third operation mode (e. g., a READ operation mode) according to an embodiment of the present disclosure.

In the READ operation mode, the second signals Sout1 to SoutN reflecting the characteristics (e. g., type) of the first signal are read out (e. g., output) from the memristor array 410.

In the READ operation mode, the memristor unit to be read may be firstly selected in the memristor array.

In an embodiment of the present disclosure, WL1 to WLN may be activated (e. g., turned on) sequentially (e. g., column by column) by the second switching circuit 440 to apply a word line voltage (e. g., 4V) to the corresponding word lines, and a ground voltage may be applied to the corresponding bit lines through the third switching circuit 470 to sequentially activate the memristor units of the corresponding columns. In this case, the read signals corresponding to the conductivity state of each memristor unit may be read sequentially from the corresponding source line.

In an embodiment of the present disclosure, the word line voltage (e. g., 4V) of the READ operation mode may be less than the word line voltage (e. g., 5V) of the PROCESS operation mode.

In some examples, in the READ operation mode, the shift register 4410 may output cyclically shifted data. For example, at the first time, the shift register 4410 may output "1000 . . . 000", at the second time, the shift register 4410 may output "0100 . . . 000" (the time corresponding to FIG. 6C), at the third time, the shift register 4410 may output "0010 . . . 000", and at the M time, the shift register 4410 may output "0000 . . . 001". At each time, the shift register 4410 generates a data signal so that one of the plurality of selectors 4430 is selected, thereby activating the memristor unit of the corresponding column.

In some embodiments, in the READ operation mode, under the control of the control circuit 400, the read signal corresponding to the activated memristor unit may be read through the output circuit 450 in response to the fourth control signal CTRL4. For example, for the source line SL1, the read signals corresponding to the memristor units (e. g., M11, M12, M13, . . . , M1M) of the first row may be sequentially read. The read signal read may then be transmitted to the output circuit 450 through the first switching circuit 430 (e. g., under the control of the first control signal CTRL1).

In one example, the output circuit 450 may directly output the read signal read from the source line as the second signal. For example, for the source line SL1, the output circuit may directly output the read signal read from the source line SL1 as the second signal Sout1.

In another example, when the output circuit 450 comprises a plurality of current type sensitive amplifiers 450-1 to 450-N, the signal may be read from the corresponding source line through the corresponding current type sensitive amplifier (e. g., by generating a read voltage and sensing the current of the corresponding source line at the read voltage), the read signal is compared with the reference current Iref to determine the quantized read signal, and the quantized read signal is used as the second signal. For example, for the source line SL1, the output circuit 450 may convert the read signal read from the source line SL1 into a current signal and compare it with the reference current Iref to determine the quantized read signal, and take the quantized read signal as the second signal Sout1.

The principle of the operation of the signal processing apparatus in FIG. 4 in various operation modes is described above. Embodiments of various operation mode switching methods will be described below in connection with FIG. 7.

Figure 7:
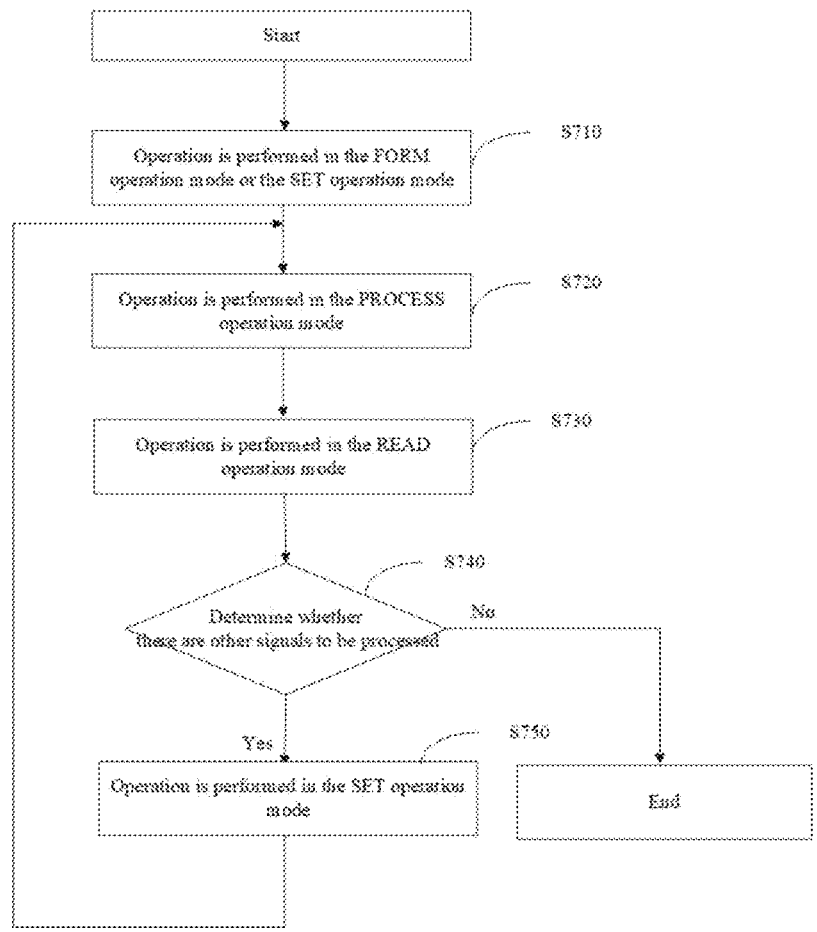
FIG. 7 illustrates a flowchart of a method of switching various operation modes according to an exemplary embodiment of the present disclosure.

FIG. 7 illustrates a flowchart of a method of switching various operation modes according to an embodiment of the present disclosure.

Referring to FIG. 7, in step S710, the operation is performed in the FORM operation mode or the SET operation mode. For example, in the FORM operation mode, the memristor array is electrically initialized (called FORM operation). After initialization, the memristor in the memristor array may be switched between high conductivity state and low conductivity state. In the SET operation mode, set the memristor array (called SET operation). Through the set operation, the memristor in the memristor array changes from a low conductivity state to a high conductivity state.

Then, in step S720, the operation is performed in the PROCESS operation mode. In the PROCESS operation mode, a plurality of first signals are respectively applied (e. g., written) to the corresponding memristor units of the memristor array to modulate the conductivity of the memristors in the memristor units. For example, by applying the first signal, the memristor in the memristor unit is reset (RESET).

After the PROCESS operation mode, the first signal is encoded into the conductivity value (or resistance value) of the memristor in the memristor unit and stored as the result of the memristor array processing the first signal. In the embodiment of the present disclosure, the memristor array encodes, compresses and retains the information of the first signal. Therefore, a second signal reflecting the characteristics of the first signal (e. g., corresponding type or corresponding continuous physical quantity) may be output from the memristor array.

Next, in step S730, it is operated in the READ operation mode. In the READ operation mode, a second signal reflecting the characteristics of the first signal (e. g., corresponding type or corresponding continuous physical quantity) is read out (e. g., output) from the memristor array.

Then, in step S740, it is determined whether there are other signals to be processed. For example, it may firstly be determined whether all segments of the first signal have been applied to the corresponding memristor unit. After the processing of the first signal has been completed, it may then continue to determine whether there are other signals to be processed. If there are other signals to be processed, switch to the SET operation mode for operation in step S750. In the SET operation mode, set the memristor array (called SET operation). Through the set operation, the memristor in the memristor array changes from low conductivity state to high conductivity state. Then, return to step S720 and switch to the PROCESS mode for operation to process the other signals similar to the first signal.

Through the operation mode and operation mode switching method according to the embodiment of the present disclosure described above, the first signal may be processed quickly and effectively to obtain a second signal based on the conductivity value of the memristor for further processing (e. g., classification or regression) without additional analog-to-digital conversion components to process the first signal. Therefore, the processing method according to the embodiment of the present disclosure has strong scalability, low computing cost and low power consumption.

As understood by those skilled in the art, the memristor array, the control circuit, the first switching circuit, the second switching circuit, the third switching circuit, the input circuit and the output circuit and any other disclosed elements described in the above various embodiments, may use one or more of central processing unit (CPU), arithmetic logic unit (ALU), digital signal processor, microcomputer, field programmable gate array (FPGA), system on chip (SoC), programmable logic unit, microprocessor and application-specific integrated circuit (ASIC). For example, the memristor array, the control circuit, the first switching circuit, the second switching circuit, the third switching circuit, the input circuit and the output circuit, and any other disclosed elements described above, may comprise processing circuits, such as hardware including logic circuits; a hardware/software combination, such as a processor executing software; or a combination of them. For example, the processing circuit may more specifically comprise, but is not limited to, a central processing unit (CPU), an arithmetic logic unit (ALU), a digital signal processor, a microcomputer, a field programmable gate array (FPGA), a system on chip (SoC), a programmable logic unit, a microprocessor, an application specific integrated circuit (ASIC), etc.

Figure 8:
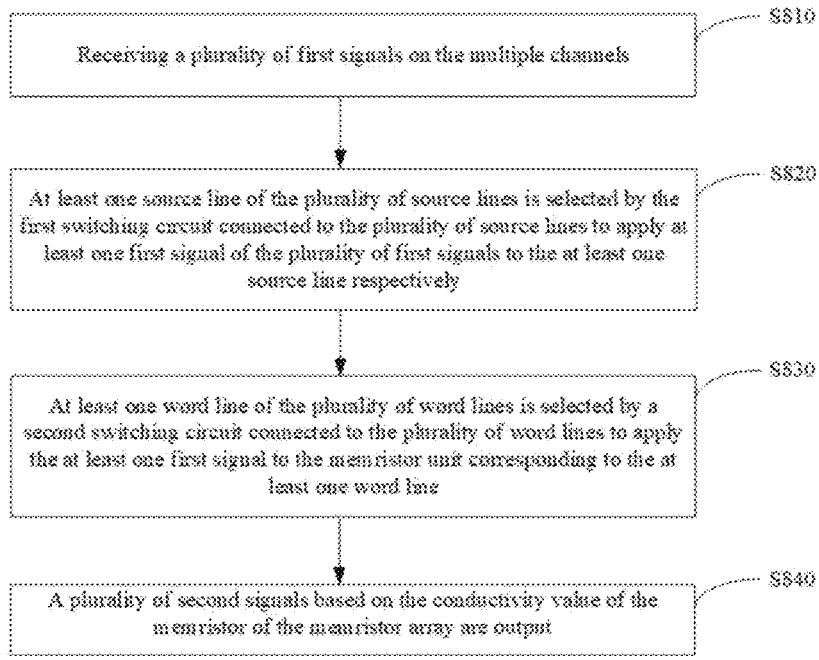
FIG. 8 illustrates a flowchart of a signal processing method according to an exemplary embodiment of the present disclosure.

FIG. 8 illustrates a flowchart of a signal processing method according to an exemplary embodiment of the present disclosure. For example, the signal processing method may be applicable to any one of the signal processing devices in the various embodiments described above. The following description will be made with reference to FIGS. 2 to 8.

In some embodiments, the signal processing apparatus comprises a memristor array, the memristor array comprises a plurality of memristor units and is connected to a plurality of source lines, a plurality of word lines and a plurality of bit lines, and each of the plurality of memristor units comprises a memristor.

Referring to FIG. 8, in step S810, a plurality of first signals on multiple channels are received.

In step S820, at least one source line of the plurality of source lines is selected by the first switching circuit connected to the plurality of source lines to apply at least one first signal of the plurality of first signals to the at least one source line respectively.

In step S830, at least one word line of the plurality of word lines is selected by a second switching circuit connected to the plurality of word lines to apply the at least one first signal to the memristor unit corresponding to the at least one word line.

In step S840, a plurality of second signals based on the conductivity values of the memristors of the memristor array are output.

In some embodiments, before the at least one first signal is applied, the plurality of word lines are selected by the second switching circuit to apply a first voltage to the memristor units corresponding to the plurality of word lines in response to the first control signal, and selecting the plurality of bit lines by the third switching circuit to apply a second voltage to the memristor units corresponding to the plurality of bit lines.

In some embodiments, applying the at least one first signal to the memristor unit corresponding to the at least one word line in step S830 comprises: in response to the second control signal, the second switch circuit sequentially selects and activates each of the at least one word line to apply the segments of the at least one first signal to the memristor unit corresponding to the at least one word line, and controls to apply a ground voltage to the plurality of bit lines.

In some embodiments, step S840 may comprise sequentially selecting and activating at least one of the plurality of word lines by the second switching circuit in response to the third control signal so that the plurality of second signals are output through the at least one source line, and control to apply a ground voltage to the plurality of bit lines.

In some embodiments, before step S810, it may comprise preprocessing each of the plurality of original signals by a preprocessing circuit to form the plurality of first signals with an amplitude within a predetermined range, and transmitting the plurality of first signals to the input circuit.

In some embodiments, the predetermined range is a resistance-change voltage range or a read voltage range of the memristor.

In some embodiments, step S840 is followed by classifying the second signals by a classifier to determine the type of the first signals.

For the embodiments of the above steps, reference may be made to the above detailed description of the signal processing apparatus according to various embodiments.

Through the signal processing method according to the embodiment of the present disclosure described above, the first signal may be processed quickly and effectively to obtain a second signal based on the resistance value of the memristor for further processing (e. g., classification or regression) without additional analog-to-digital conversion components to process the first signal. Therefore, the processing method according to the embodiment of the present disclosure has strong scalability, low computing cost and low power consumption.

An exemplary application of an embodiment of the present disclosure is described below in combination with FIGS. 9-13.

In some embodiments, as described above, the plurality of first signals on the multiple channels may be multi-channel signals obtained by the multi-channel signal acquisition device, such as multi-channel neural signals (e. g., multi-channel brain electrical signals). In addition, the first signal may be a voltage signal.

When the first signal is a neural signal, depending on the specific application (e.g., in epilepsy prediction), it may be necessary to determine whether the type of the first signal is the first type (e. g., Interictal type) or the second type (Preictal type) different from the first type.

In some embodiments, the first signal may be processed to obtain a second signal by a signal processing apparatus or a signal processing method of an embodiment of the present disclosure, and the second signal may be classified to obtain a type of the first signal.

Figure 9:
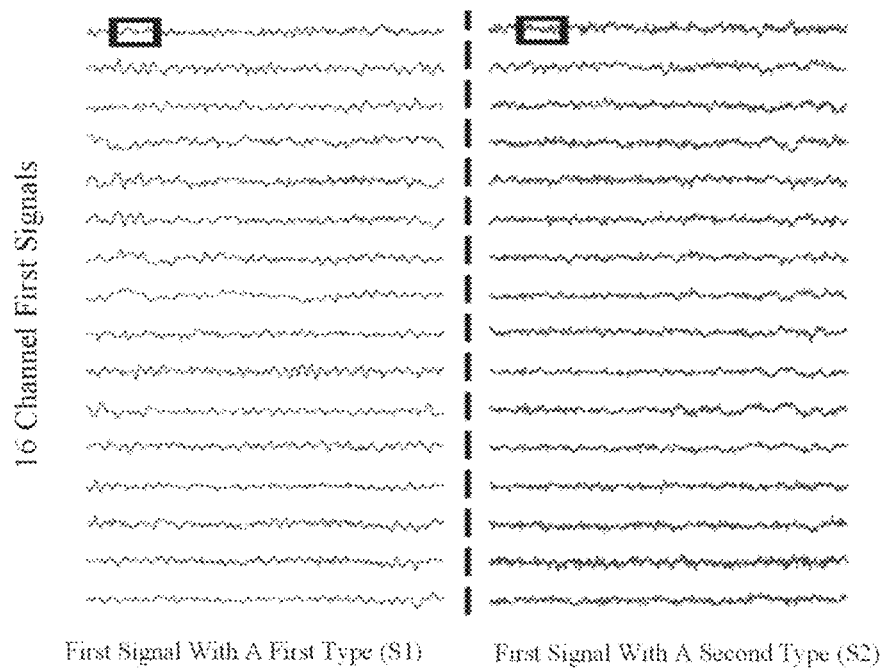
FIG. 9 illustrates schematic diagrams of a first signal having a first type (represented by S1) and a first signal having a second type (represented by S2) to be processed according to an exemplary embodiment of the present disclosure, respectively.
Figure 10:
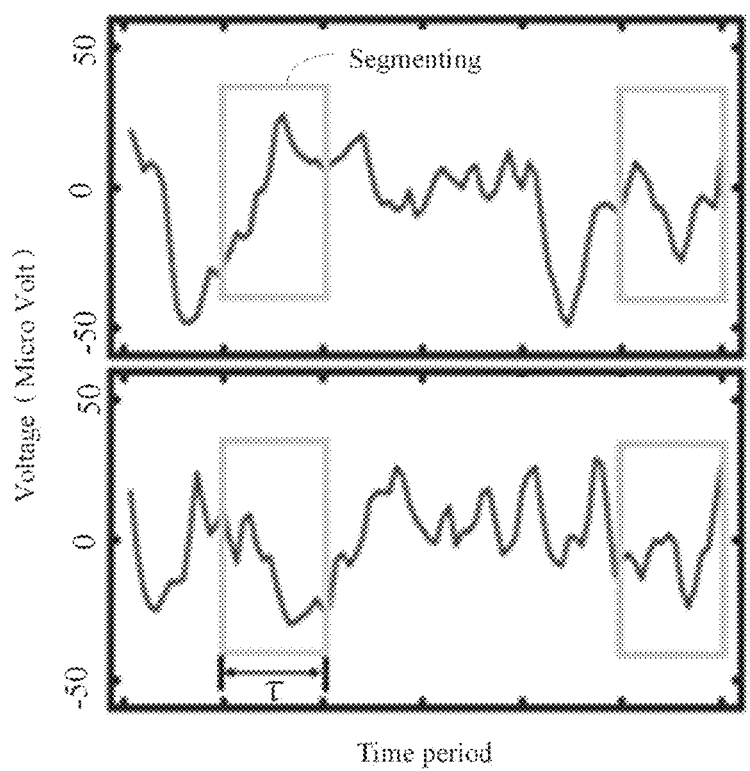
FIG. 10 illustrates a schematic diagram of segmenting a first signal during processing according to an exemplary embodiment of the present disclosure.
Figure 11:
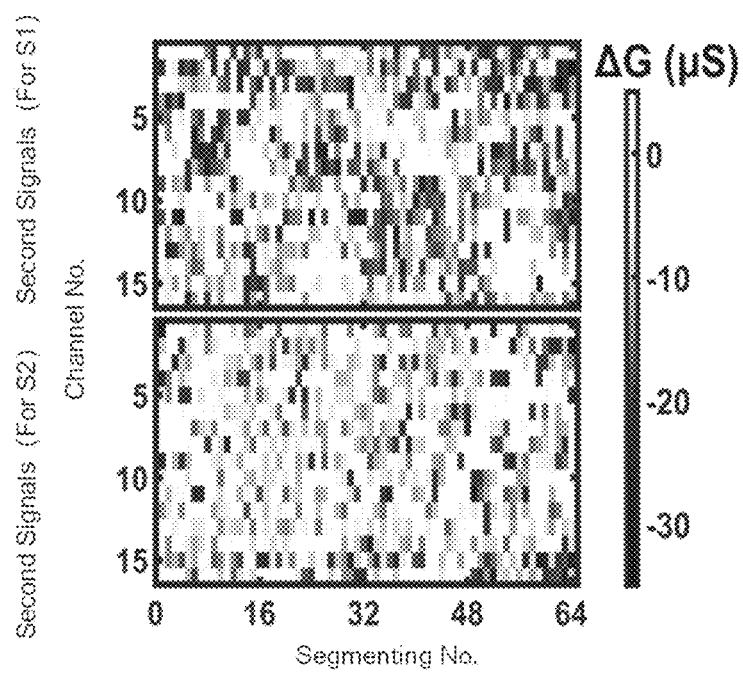
FIG. 11 illustrates a diagram of a second signal based on the resistance distribution of the memristor and obtained after processing the first signal according to an exemplary embodiment of the present disclosure.
Figure 12A:
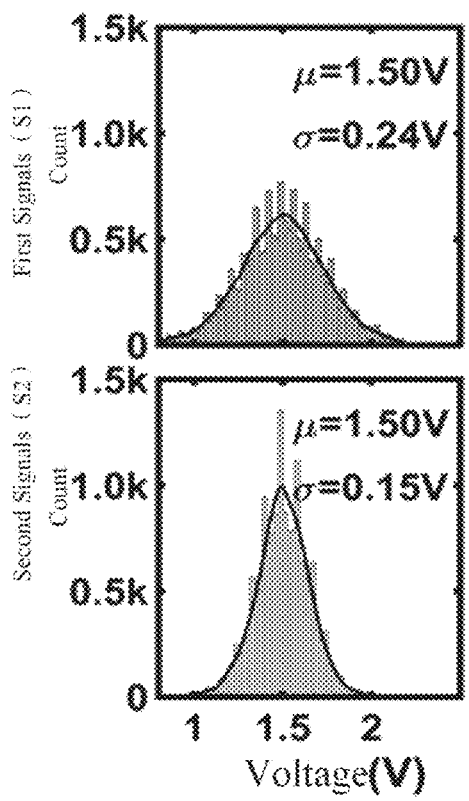
FIGS. 12A and 12B illustrate schematic diagrams of the distribution of an input first signal and an output second signal according to an exemplary embodiment of the present disclosure, respectively.
Figure 12B:
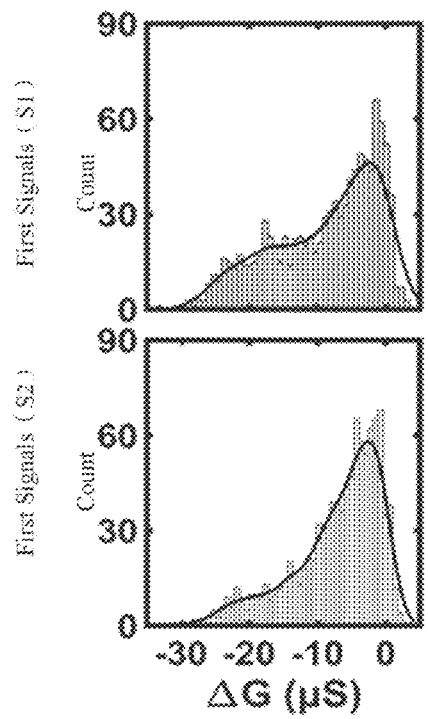

FIG. 9 illustrates schematic diagrams of a first signal with a first type (represented by S1) and a first signal with a second type (represented by S2) to be processed, respectively. Referring to FIG. 9, both the first signal with the first type and the first signal with the second type are 16 channel signals. In order to process the first signal, a signal processing apparatus having a memristor array with a size of 16*64 is used in an exemplary application. FIG. 10 illustrates a schematic diagram of segmenting a first signal during processing. FIG. 11 illustrates a schematic diagram of a second signal based on the resistance distribution of the memristor obtained after processing the first signal. In FIG. 11, ΔG represents the change amount in the conductivity value of the memristor in the memristor unit corresponding to a second signal. FIGS. 12A and 12B illustrate schematic diagrams of the distribution of the input first signal and the output second signal (based on the conductivity value of the memristor), respectively. In FIG. 12A, the vertical axis represents the statistical count of the number of pulse amplitudes for one (16 channels, 960 sampling points per channel) input voltage, and 1K represents 1000. In FIG. 12B, the vertical axis represents the statistical count of the corresponding number of 1024 ΔGs (16 channels*64, 64 devices per channel, a total of 1024 devices. Each device corresponds to 15 sampling points). Referring to FIG. 12A, for the distribution of the first signal (S1) having the first type, the mean value is μ 1.5V, the variance σ is 0.24V. Referring to FIG. 12B, for the distribution of the first signal (S2) having the second type, the mean value is μ 1.5V, and the variance σ is 0.15V.

Figure 13:
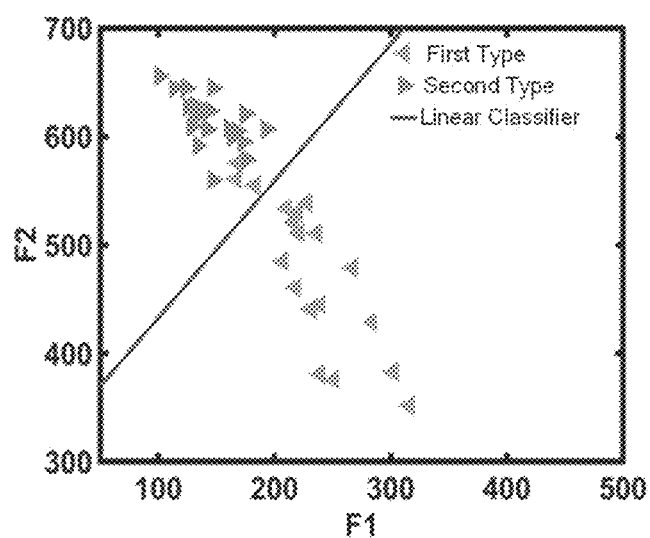
FIG. 13 illustrates a schematic diagram of a classification result according to an exemplary embodiment of the present disclosure.

After obtaining the second signal, the second signal may be classified to obtain the type of the first signal. For the first and second signals distributed in FIGS. 12A and 12B, for example, a linear classifier may be used to obtain the classification results illustrated in FIG. 13. In FIG. 13, F1 indicates the number of memristor units with the change of conductivity value Δ G in the interval [−25 μS (micro Siemens), −15 μS] and F2 indicates the number of memristor units with the change of conductivity value ΔG in the interval [−10 μS, 0 μS]. The classification result may be determined based on the number of memristor units in the corresponding interval. It should be noted that other more appropriate intervals may be selected to achieve better classification effect. By adopting the signal processing apparatus or signal processing method according to the embodiment of the present disclosure, the first signal is processed without an analog-to-digital converter to obtain a second signal that may be classified. As may be seen from FIGS. 12A and 12B, the second signal may be effectively classified to obtain the type of the first signal.

For the present disclosure, the following need to be explained:
 (1) The drawings of the embodiments of the present disclosure only relate to the structures related to the embodiments of the present disclosure, and other structures may refer to the common design.
 (2) Without conflict, the embodiments of the present disclosure and the features in the embodiments may be combined with each other to obtain a new embodiment.

The above is only an exemplary embodiment of the invention and is not used to limit the scope of protection of the invention, and the scope of the invention is determined by the appended claims.

What is claimed is:

1. A signal processing apparatus, comprising:
 a memristor array, comprising a plurality of memristor units and connected to a plurality of source lines, a plurality of word lines and a plurality of bit lines, wherein each of the plurality of memristor units comprises a memristor;
 an input circuit, configured to receive a plurality of first signals on a plurality of channels;
 a first switching circuit, connected with the plurality of source lines;
 a second switching circuit, connected with the plurality of word lines;
 an output circuit, connected with the plurality of source lines; and
 a control circuit, configured to:
  control the first switching circuit to select at least one source line of the plurality of source lines to apply at least one first signal of the plurality of first signals to the at least one source line, respectively,
  control the second switching circuit to select and activate at least one word line of the plurality of word lines to apply the at least one first signal to the memristor unit corresponding to the at least one word line, and
  control the output circuit to output a plurality of second signals based on conductivity values of memristors of the memristor array, wherein the first switching circuit comprises a plurality of first selectors, and the second switching circuit comprises a plurality of second selectors,
 wherein each of the plurality of first selectors is configured to select a corresponding source line of the plurality of source lines under a control of the control circuit to apply a corresponding first signal of the plurality of first signals to the corresponding source line,
 wherein each of the plurality of second selectors is configured to select and activate a corresponding word line of the plurality of word lines under a control of the control circuit to apply a corresponding first signal of the at least one first signal to the memristor unit corresponding to the corresponding word line.

2. The signal processing apparatus according to claim 1, further comprising:
 a third switching circuit, connected with the plurality of bit lines, wherein before the at least one first signal is applied, the control circuit is further configured, in a first operation mode, to:
  control the second switching circuit to select the plurality of word lines to apply a first voltage to the memristor units corresponding to the plurality of word lines, and
  control the third switching circuit to select the plurality of bit lines to apply a second voltage to the memristor units corresponding to the plurality of bit lines.

3. The signal processing apparatus according to claim 1, wherein the control circuit is further configured, in a second operation mode, to control the second switching circuit to sequentially select and activate each of the at least one word line, so as to apply segments of the at least one first signal to the memristor unit corresponding to the at least one word line respectively, and control to apply a ground voltage to the plurality of bit lines.

4. The signal processing apparatus according to claim 1, wherein the control circuit is further configured, in a third operation mode, to control the second switching circuit to sequentially select and activate the at least one word line of the plurality of word lines, so that the output circuit outputs the plurality of second signals through the at least one source line, and control to apply a ground voltage to the plurality of bit lines.

5. The signal processing apparatus according to claim 2, wherein the control circuit is further configured, in a fourth operation mode, to:
 control the second switching circuit to select the plurality of word lines to apply a first voltage to the memristor units corresponding to the plurality of word lines, and
 control the third switching circuit to select the plurality of bit lines to apply a second voltage to the memristor units corresponding to the plurality of bit lines.

6. The signal processing apparatus according to claim 1, wherein a number of the at least one first signal is greater than or equal to 2, and
 wherein the control circuit is configured to:
  control the first switching circuit to select at least one source line of the plurality of source lines to apply each first signal of the at least one first signal to a corresponding source line, respectively, and control the second switching circuit to select and activate at least one word line of the plurality of word lines to apply each first signal of the at least one first signal to the memristor unit corresponding to a corresponding word line.

7. The signal processing apparatus according to claim 1, further comprising a preprocessing circuit, wherein the preprocessing circuit is configured to preprocess each original signal of a plurality of original signals to form the plurality of first signals with an amplitude within a predetermined range, and transmit the plurality of first signals to the input circuit.

8. The signal processing apparatus according to claim 7, wherein the predetermined range is a resistance-change voltage range or a read voltage range of the memristor.

9. The signal processing apparatus according to claim 7, wherein the preprocessing circuit comprises an amplification circuit and a bias circuit,
wherein the bias circuit is configured to provide a bias signal, and the amplification circuit is configured to process the original signal based on the bias signal to form the plurality of first signals with the amplitude within the predetermined range.

10. The signal processing apparatus according to claim 1, further comprising a classifier or regressor,
wherein the classifier or regressor is configured to classify or regress the second signals to determine a type of the first signals or a magnitude of a continuous physical quantity corresponding to the first signals.

11. A signal processing apparatus, comprising:
a memristor array, comprising a plurality of memristor units and connected to a plurality of source lines, a plurality of word lines and a plurality of bit lines, wherein each of the plurality of memristor units comprises a memristor;
an input circuit, configured to receive a plurality of first signals on a plurality of channels;
a first switching circuit, connected with the plurality of source lines;
a second switching circuit, connected with the plurality of word lines;
an output circuit, connected with the plurality of source lines; and
a control circuit, configured to:
control the first switching circuit to select at least one source line of the plurality of source lines to apply at least one first signal of the plurality of first signals to the at least one source line, respectively,
control the second switching circuit to select and activate at least one word line of the plurality of word lines to apply the at least one first signal to the memristor unit corresponding to the at least one word line, and
control the output circuit to output a plurality of second signals based on conductivity values of memristors of the memristor array, wherein the output circuit comprises a plurality of current type sensitive amplifiers, and each of the plurality of current type sensitive amplifiers is configured to determine a corresponding second signal of the plurality of second signals based on a reference current and a signal read from a corresponding source line.

12. A signal processing method, applicable to a signal processing apparatus, the signal processing apparatus comprising:
a memristor array, the memristor array comprising a plurality of memristor units and being connected to a plurality of source lines, a plurality of word lines and a plurality of bit lines, each of the plurality of memristor units comprising a memristor,
an input circuit, configured to receive a plurality of first signals on a plurality of channels;
a first switching circuit, connected with the plurality of source lines;
a second switching circuit, connected with the plurality of word lines;
an output circuit, connected with the plurality of source lines; and
a control circuit, configured to:
control the first switching circuit to select at least one source line of the plurality of source lines to apply at least one first signal of the plurality of first signals to the at least one source line, respectively,
control the second switching circuit to select and activate at least one word line of the plurality of word lines to apply the at least one first signal to the memristor unit corresponding to the at least one word line, and
control the output circuit to output a plurality of second signals based on conductivity values of memristors of the memristor array,
wherein the first switching circuit comprises a plurality of first selectors, and the second switching circuit comprises a plurality of second selectors,
wherein each of the plurality of first selectors is configured to select a corresponding source line of the plurality of source lines under a control of the control circuit to apply a corresponding first signal of the plurality of first signals to the corresponding source line,
wherein each of the plurality of second selectors is configured to select and activate a corresponding word line of the plurality of word lines under a control of the control circuit to apply a corresponding first signal of the at least one first signal to the memristor unit corresponding to the corresponding word line,
the signal processing method comprising:
receiving a plurality of first signals on a plurality of channels;
selecting at least one source line of the plurality of source lines to apply at least one first signal of the plurality of first signals to the at least one source line respectively by a first switching circuit connected with the plurality of source lines;
selecting at least one word line of the plurality of word lines to apply the at least one first signal to the memristor unit corresponding to the at least one word line by a second switching circuit connected with the plurality of word lines; and
outputting a plurality of second signals based on conductivity values of memristors of the memristor array.

13. The method according to claim 12, in response to a first control signal, before the at least one first signal is applied, further comprising:
selecting the plurality of word lines to apply a first voltage to the memristor units corresponding to the plurality of word lines by the second switching circuit, and
select the plurality of bit lines to apply a second voltage to the memristor units corresponding to the plurality of bit lines by a third switching circuit.

14. The method according to claim 12, wherein applying the at least one first signal to the memristor unit corresponding to the at least one word line comprises:
in response to a second control signal, selecting and activating each of the at least one word line so as to apply segments of the at least one first signal to the memristor unit corresponding to the at least one word line respectively by the second switching circuit, and applying a ground voltage to the plurality of bit lines.

15. The method according to claim 12, wherein outputting the plurality of second signals based on the conductivity values of the memristors of the memristor array comprises:

in response to a third control signal, selecting and activating the at least one word line of the plurality of word lines sequentially by the second switching circuit, so as to output the plurality of second signals through the at least one source line, and applying a ground voltage to the plurality of bit lines.

16. The method according to claim 12, before receiving a plurality of first signals by an input circuit, further comprising:

preprocessing each original signal of a plurality of original signals to form the plurality of first signals with an amplitude within a predetermined range by a preprocessing circuit, and transmitting the plurality of first signals to the input circuit.

17. The method according to claim 16, wherein the predetermined range is a resistance-change voltage range or a read voltage range of the memristor.

18. The method according to claim 12, wherein a number of the at least one first signal is greater than or equal to 2, wherein selecting the at least one source line of the plurality of source lines to apply the at least one first signal of the plurality of first signals to the at least one source line respectively by the first switching circuit connected with the plurality of source lines comprises: controlling the first switching circuit to select the at least one source line of the plurality of source lines to apply each first signal of the at least one first signal to a corresponding source line respectively, and selecting the at least one word line of the plurality of word lines to apply the at least one first signal to the memristor unit corresponding to the at least one word line by the second switching circuit connected with the plurality of word lines comprises: controlling the second switching circuit to select and activate the at least one word line of the plurality of word lines to apply each first signal of the at least one first signal to the memristor unit corresponding to a corresponding word line.

19. The method according to claim 12, further comprising:

classifying or regressing the second signals to determine a type of the first signals or a magnitude of a continuous physical quantity corresponding to the first signals by a classifier or regressor.

* * * * *